United States Patent [19]
Minai et al.

[11] Patent Number: 5,332,675
[45] Date of Patent: Jul. 26, 1994

[54] OPTICALLY ACTIVE AROMATIC CARBOXYLIC ACID DERIVATIVES AND PROCESS FOR PRODUCING THE SAME

[75] Inventors: Masayoshi Minai, Moriyama; Takayuki Higashii, Kishiwada, both of Japan

[73] Assignee: Sumitomo Chemical Company, Limited, Osaka, Japan

[21] Appl. No.: 920,159

[22] Filed: Jul. 27, 1992

Related U.S. Application Data

[60] Continuation of Ser. No. 667,745, Mar. 11, 1991, abandoned, which is a division of Ser. No. 186,020, Apr. 25, 1988, Pat. No. 5,019,298.

[30] Foreign Application Priority Data

Apr. 30, 1987 [JP] Japan ................... 62-109513
Sep. 22, 1987 [JP] Japan ................... 62-238191
Mar. 4, 1988 [JP] Japan ................... 63-52454

[51] Int. Cl.$^5$ ................ C12P 41/00; C07C 69/76
[52] U.S. Cl. ................... 435/280; 560/55; 560/59; 560/66; 560/73
[58] Field of Search ............. 560/59, 64, 66; 435/280

[56] References Cited

U.S. PATENT DOCUMENTS 4,016,186  4/1977  Kondo .................... 560/66
4,962,031  10/1990  Yoshida et al. ........... 435/280

FOREIGN PATENT DOCUMENTS 59119590  1/1986  Japan .
2181429  4/1987  United Kingdom .

OTHER PUBLICATIONS

Okumura; S., BBA 575: 158–165 (1979).
Cambou, B., Biotech and Bioengineering XXVI: 1449–54 (1984).
Lazar, G. et al., in Proceedings of the World Conference on Emerging Technologies in the Fats and Oil (List continued on next page.)

*Primary Examiner*—Douglas W. Robinson
*Assistant Examiner*—S. Saucier
*Attorney, Agent, or Firm*—Stevens, Davis, Miller & Mosher

[57] ABSTRACT

Disclosed are optically active aromatic carboxylic acid derivatives represented by the formula (I):

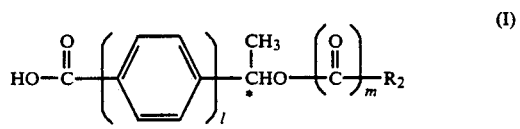

(wherein $R_2$ represents an alkoxyalkyl group having 1 to 20 carbon atoms or an alkyl group having 1 to 20 carbon atoms, which alkyl group may be substituted with a halogen atom; l represents a number of 1 or 2; m represents a number of 0 or 1; and * indicates asymmetric carbon atom) and a process for producing such derivatives through the following reaction steps:

Ketones $\xrightarrow{\text{reduction}}$ alcohols $\xrightarrow{\text{esterification}}$ esters $\xrightarrow[\text{hydrolysis}]{\text{asymmetric}}$ optically active alcohols $\xrightarrow[\text{alkylating agent or acylating reagent (VI)}]{\text{alkylation or acylation}}$ optically active benzene derivatives $\xrightarrow[\text{or hydrogenation}]{\text{hydrolysis}}$ optically active aromatic carboxylic acid derivatives (I).

A process for the hydrolysis of ester derivatives of (I) using esterase is described.

The optically active aromatic carboxylic acid derivatives represented by the above-described formula (I) are useful as a liquid crystal material and can be also utilized as an intermediate for the preparation of pharmaceuticals, agricultural chemicals and the like.

8 Claims, No Drawings

OTHER PUBLICATIONS

Industry, ed. Baldwin published by American Oil Chemist's Society, pp. 346–354 (1986).

Jones et al, Tetrahedron 42:3351–3403 (1986).

Baratti et al, in Proceedings of the World Conference on Emerging Technologies in the Fats and Oils Industry, ed. Baldwin, pp. 355–358 (1986).

Eichberger, G., Monatshefte für Chemie 116:1233–1236 (1985).

J. Org. Chem., 45 (13) 2581–2585 (1980).

J. Org. Chem., 24, 549–551 (1959).

Chemical Abstracts, vol. 53, No. 22, Nov. 25, 1959, E. D. Bergmann et al, Abstract No. 21786H, "P-Vinylbenzoic Acid and P-Vinylphenylacetic . . .".

OPTICALLY ACTIVE AROMATIC CARBOXYLIC ACID DERIVATIVES AND PROCESS FOR PRODUCING THE SAME

This application is a continuation of application Ser. No. 07/667,745, filed Mar. 11, 1991 now abandoned, which in turn is a division of application Ser. No. 07/186,020, filed Apr. 25, 1988 now U.S. Pat. No. 5,019,298.

BACKGROUND OF THE INVENTION

1. Field of the Invention

The present invention relates to a novel and useful optically active aromatic carboxylic acid derivatives represented by the following formula (I) and the processes for producing such derivatives.

Such optically active aromatic carboxylic acid derivatives, let alone their preparation process, have been totally unknown in the art.

2. Description of the Prior Art

E. D. Bergmann, J. Org. Chem., 24 549 (1959) describes the compound represented by the general formula, HOOC—⟨benzene⟩—CHOC$_2$H$_5$ with CH$_3$ substituent, which is, however, racemic compound and not disclosed or any practical application at all.

In addition, said compound cannot be utilized as an intermediate of a ferroelectric liquid crystal compound because of being racemic compound, whereas the compound of the present invention can readily be derived to such a ferroelectric liquid crystal compound.

For example, the following prior art (I') is a process for preparing an optically active aromatic carboxylic acid derivative by means of introducing an active alkyl group into phenol, and the prior art (II') is that by means of ethyl-etherification by applying ethanol and an alkali to α-bromoethyl group of the benzene carboxylic acid, whereas the present invention is a process for obtaining an optically active aromatic carboxylic acid derivative by alkylating an optically active alcohol obtained from asymmetric hydrolysis of the corresponding racemic ester and then debenzylating or de-(lower) alkylating. Since said optically active alcohols has the asymmetric carbon atom directly bonded to benzene ring, needless to say, the produced aromatic carboxylic acid derivatives become optically active. Accordingly, the process of the present invention is entirely different from the prior art processes.

(I') HOOC—⟨benzene⟩—OH ⟶

HOOC—⟨benzene⟩$_l$—OCHC$_n$H$_{2n+1}$ with CH$_3$ substituent (*)

wherein l is 1 or 2 and * indicate asymmetric carbon atom.

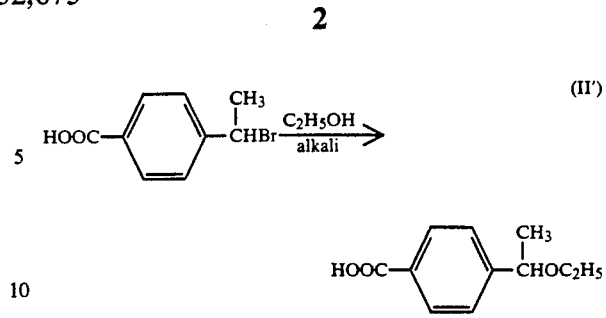

(II') HOOC—⟨benzene⟩—CHBr with CH$_3$ substituent $\xrightarrow{C_2H_5OH, alkali}$ HOOC—⟨benzene⟩—CHOC$_2$H$_5$ with CH$_3$ substituent

SUMMARY OF THE INVENTION

This invention provides optically active aromatic carboxylic acid derivatives represented by the formula (I):

$$HO-\overset{O}{\overset{\|}{C}}-⟨benzene⟩_l-\overset{CH_3}{\underset{*}{C}}HO-(\overset{O}{\overset{\|}{C}})_m-R_2 \quad (I)$$

wherein R$_2$ represents an alkoxyalkyl group having 1 to 20 carbon atoms or an alkyl group having 1 to 20 carbon atoms, which alkyl group may be substituted with a halogen atom; l represents a number of 1 or 2; m represents a number of 0 or 1; and * indicates asymmetric carbon atom and a process for producing such derivatives, through the reaction steps as shown in the following reaction scheme:

Ketones of formula (II) $\xrightarrow{\text{reduction}}$ alcohols of formula (III) $\xrightarrow{\text{esterification}}$ esters of formula (IV) $\xrightarrow[\text{hydrosis}]{\text{asymmetric}}$ optically active alcohols of formula (V) $\xrightarrow[\text{alkylating or acylating reagent (VI)}]{\text{alkylation or acylation}}$ optically active benzene derivatives (VII) $\xrightarrow[\text{or hydrogenation}]{\text{hydrolysis}}$ optically active aromatic carboxylic acid derivatives (I).

The optically active aromatic carboxylic acid derivatives represented by the above-described formula (I) are useful as a liquid crystal material and can be also utilized as an intermediate for the preparation of pharmaceuticals, agricultural chemicals and the like.

DETAILED DISCLOSURE OF THE INVENTION

The present invention provides optically active aromatic carboxylic acid derivatives represented by the formula (I) and also processes for producing the same, which processes comprise steps 1-5, steps 2-5, steps 3-5, steps 4-5 and step 5, respectively, which are described below:

Step 1:

Ketones represented by the formula (II):

(wherein R$_1$ represents a lower alkyl group or

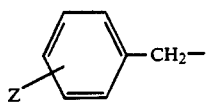

wherein Z represents a hydrogen atom, a halogen atom or a lower alkyl or lower alkoxyl group; and l represents a number of 1 or 2) are reduced by using a reducing reagent to form alcohols represented by the formula (III):

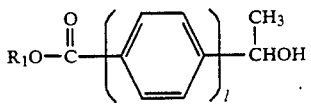

wherein R$_1$ and l have the same meanings as defined above.

Step 2:

The alcohols of the formula (III) obtained in the step 1 are reacted with lower alkylcarboxylic acids to produce esters represented by the formula (IV):

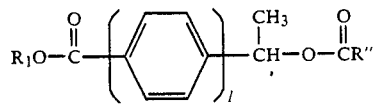

wherein R$_1$ and l is as defined above, and R″ each represents a lower alkyl group.

Step 3:

The esters of the formula (IV) obtained in the step 2 are subjected to asymmetric hydrolysis by using an esterase having the ability to hydrolyze one of the enantiomers of said esters to obtain the optically active alcohols represented by the formula (V):

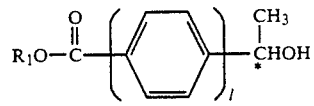

wherein R$_1$ and l have the same meanings as defined above, and * indicates asymmetric carbon atom.

Step 4:

The optically active alcohols of the formula (V) obtained in step 3 are condensed with an alkylating reagent or an acylating reagent represented by the formula (VI):

R$_2$—X  (VI)

(wherein R$_2$ represents an alkoxyalkyl group having 1 to 20 carbon atoms or an alkyl group having 1 to 20 carbon atoms, which alkyl group may be substituted with a halogen atom; and X represents a halogen atom, —OSO$_2$R‴ or

wherein R‴ represents a lower alkyl group or a phenyl group which may be substituted, and Y represents a hydroxyl group, a halogen atom or R$_2$COO) to produce the optically active benzene derivatives represented by the formula (VII):

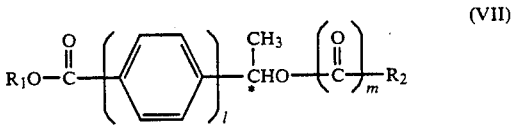

(wherein R$_1$, R$_2$, l and * have the same meanings as defined above, and m is 0 or 1).

Step 5:

The optically active benzene derivatives of the formula (VII) obtained in step 4 are hydrolyzed under an alkaline condition or debenzylated by catalytic hydrogenation to obtain the optically active aromatic carboxylic acid derivatives represented by the formula (I).

The optically active benzene derivatives represented by the formula (VII) are also the novel compounds, and they are very useful as a liquid crystal material or as an intermediate for the preparation thereof.

The present invention will be further described in detail below.

The ketones (II) used as starting material in step 1 can be easily produced by reacting acetylcarboxylic acids with a lower alkylating reagent or benzylating reagent:

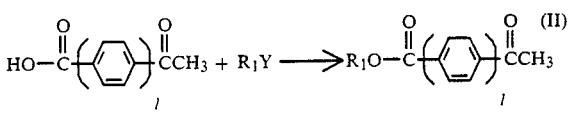

wherein Y represents a halogen atom or a hydroxyl group and so on.

Reduction of ketones (II) is effected by using a reducing agent which is capable of reducing ketones into alcohols.

Preferred examples of such reducing agent are sodium borohydride, zinc borohydride, aluminum isopropoxide, lithium-tri-t-butoxyaluminum hydride, lithium-tri-s-butylborohydride, borane, lithium aluminum hydride-silica gel, alkali metal-ammonia and the like. Such reducing agent needs to be used in an amount of at least one equivalent, usually 1 to 10 equivalents, to the starting ketone (II).

This reaction is usually carried out in a solvent. As the solvent, there can be used those which are inert to the reaction, for example, water, ethers such as tetrahydrofuran, dioxane, ethyl ether, etc.; esters such as ethyl acetate; alcohols such as methanol, ethanol, n-propyl alcohol, isopropyl alcohol, etc.; aromatic hydrocarbons such as toluene, benzene, etc.; and halogenated hydrocarbons such as chloroform, dichloromethane, etc. These solvents can be used each alone or in a mixture of two or more.

The reaction temperature may be selected from the range from −30° C. to 100° C., but the range from −20° C. to 90° C. is preferred.

The reaction mixture is subjected to such operations as separation, concentration, distillation, crystallization, etc., to give alcohols (III) in a high yield. It is not always necessary to isolate alcohols (III) for obtaining esters (IV) in the next step; the reaction mixture may be subjected immediately to the treatment of the next step.

The reaction for producing esters (IV) from alcohols (III) (step 2) comprises reacting alcohols (III) with lower alkylcarboxylic acid derivatives to acylate said alcohols.

As the lower alkylcarboxylic acid derivatives used in this acylation reaction, there are used acid anhydrides or acid halides of lower alkylcarboxylic acids, such as acetic anhydride, acetyl chloride or bromide, propionic anhydride, propionic acid chloride or bromide, butyryl chloride or bromide, valeroyl chloride or bromide, and the like.

The amount of the lower alkylcarboxylic acid derivative used in this reaction should be not less than one equivalent to the alcohol (III). Its upper shreshold amount is not defined, but it is preferably four equivalents to said alcohol (III).

This reaction is carried out in the presence or absence of a solvent by using a catalyst.

In case of using a solvent in this reaction, such solvent should be the one which is inert to the reaction, for example, ethers, ketones, aliphatic or aromatic hydrocarbons, halogenated hydrocarbons, esters and aprotic polar solvents such as tetrahydrofuran, ethyl ether, acetone, methyl ethyl ketone, toluene, benzene, hexane, chlorobenzene, dichloromethane, dichloroethane, chloroform, carbon tetrachloride, ethylacetate, dimethylformamide, acetonitrile, etc. These solvents may be used either singly or in admixture. The amount of the solvent(s) to be used in the reaction is not specified.

As the catalyst, there can be used organic or inorganic basic materials such as dimethylaminopyridine, triethylamine, tri-n-butylamine, pyridine, picoline, imidazole, sodium carbonate, potassium hydrogencarbonate and the like. It is also possible to use organic or inorganic acids such as toluenesulfonic acid, methanesulfonic acid, sulfuric acid, etc.

The amount of the catalyst to be used can not be specified as it varies depending on the type of the lower alkylcarboxylic acid and its derivatives, combination thereof with the catalyst used and other factors, but in case of using an acid halide as the lower alkylcarboxylic acid and its derivatives, the catalyst is used in an amount of one equivalent or more to such acid halide.

The reaction temperature is usually in the range from −30° C. to 100° C., preferably −20° C. to 90° C.

The reaction time is not defined. The moment at which the starting alcohol (III) has vanished may be taken as the end point of the reaction.

The reaction is followed by the ordinary separating operations such as extraction, separation of liquid phase, concentration, recrystallization, etc., by which esters (IV) can be obtained in a high yield. If necessary, the resulting product may be purified by column chromatography or other means, but the reaction mixture may be subjected in the form as it is to the treatment of the next step.

The reaction for obtaining optical active alcohols (V) from said esters (IV) (step 3) comprises reacting (asymmetric hydrolysis) one of the enantiomers of said esters by using an esterase having the ability to hydrolyze one of the enantiomers of said esters.

As the microorganism producing the esterase used in the above reaction, there can be employed any of those microorganisms which are capable of producing an esterase having the ability to effectuate asymmetric hydrolysis of esters (IV).

When the term "esterase" is used in this invention, it means esterases of the broad sense including lipase.

Examples of such esterase-producing microorganisms are those belonging to the genera Enterobacter, Arthrobacter, Brevibacterium, Pseudomonas, Alcaligenes, Micrococcus, Chromobacterium, Microbacterium, Corynebacterium, Bacillus, Lactobacillus, Trichoderma, Candida, Saccharomyces, Rhodotorula, Cryptoccus, Torulopsis, Pichia, Penicillium, Aspergillus, Rhizopus, Mucor, Aureobasidium, Actinomucor, Nocardia, Streptomyces, Hansenula and Achromobacter.

Culture of these microorganisms is usually accomplished according to a conventional method. For example, when liquid culture is carried out, a culture medium can be obtained in the following manner.

A sterilized liquid medium [a malt extract-yeast extract medium (prepared by dissolving 5 g of peptone, 10 g of glucose, 3 g of malt extract and 3 g of yeast extract in 1 liter of water, with pH adjusted to 6.5) for culture of mold and yeast fungi) or a sweetened bouillon medium (prepared by dissolving 10 g of glucose, 5 g of peptone, 5 g of meat extract and 3 g of NaCl in 1 liter of water, with pH adjusted to 7.2) for culture of bacteria] is inoculated with microorganisms and subjected to reciprocal shaking culture usually at 30°–40° C. for 1-3 days. If necessary, solid culture may be employed.

Some of the esterases usable in the reaction of this invention are commercially available. The following can be mentioned as examples of such commercially available esterases: Lipase P (lipase derived from the Pseudomonas, available from Amano Pharmaceutical Co., Ltd.), Lipase AP (lipase derived from the Aspergillus, available from Amano Pharmaceutical Co., Ltd.), Lipase M-AP (lipase derived from the Mucor, available from Amano Pharmaceutical Co., Ltd.), Lipase MY (lipase derived from Candida Cylindlasse, available from Meito Sangyo Co., Ltd.), Lipase PL (lipase derived from the Alcaligenes, available from Meito Sangyo Co., Ltd.), Lipase AL (lipase derived from the Achromobacter, available from Meito Sangyo Co., Ltd.), Lipase Godo BSL (lipase derived from the Arthrobacter, available from Godo Shusei Co., Ltd.), lipase derived from the Chromobacterium (available from Toyo Brewage Co., Ltd.), Talipase (lipase derived from the Rhizopus Delemar, available from Tanabe Pharmaceutical Co., Ltd.), and Lipase Saiken (lipase derived from the Rhizopus, available from Osaka Bacterial Research Institute).

It is also possible to use animal and plant esterases such as steapsin, pancreatin, swine liver esterase, wheat germ, esterase, etc.

Enzymes obtained from animals, plants and microorganisms can be used as esterase in the reaction of this invention, and such enzymes can be used in the various forms as desired, such as purified enzyme, crude enzyme, enzyme-containing substance, liquid culture of microorganism, culture, bacterial body, culture filtrate and their treated products. Combinations of enzymes and microorgansims are also usable. Further, fixed enzymes or fixed bacterial bodies, in which the enzymes or bacterial bodies have been fixed to a resin, etc., can be used.

The asymmetric hydrolysis reaction is carried out by vigorously stirring a mixture of the starting ester (IV) and said enzyme or microorganism usually in a buffer solution.

The buffer solution used in this reaction may be a commonly used buffer solution of an inorganic acid salt such as sodium phosphate, potassium phosphate, etc., or an organic acid salt such as sodium acetate, sodium citrate, etc. The pH of the buffer solution is preferably 8 to 11 in the case of cultures of alkaliphilic bacteria or alkaline esterases and 5 to 8 in the case of cultures of non-alkaliphilic microorganisms or esterases having no alkali resistance. The concentration of the buffer solution is usually in the range of 0.05 to 2M, preferably 0.05 to 0.5M.

The reaction temperature is usually 10° to 60° C. and the reaction time is generally 3 to 70 hours, though they are not defined in these ranges.

After such hydrolysis reaction has been completed, the optical active alcohol (V) which is the hydrolyzate and optical active ester (non-hydrolyzed optical active substance in said starting ester (IV)) are separated by extracting the reaction solution with a solvent such as methyl isobutyl ketone, ethyl acetate, ethyl ether, etc., distilling off the solvent from the organic layer and subjecting the concentrated residue to column chromatography, or by other means.

The optical active ester obtained here may if necessary be further hydrolyzed to be turned into an optical active alcohol which is an enantiomer of the previously obtained optical active alcohol (V).

In case of using lipase belonging to the Pseudomonas or Arthrobacter in said asymmetric hydrolysis reaction, there can be obtained an optical active alcohol with a relatively high optical purity.

In this hydrolysis reaction, it is also possible to use an organic solvent inert to the reaction, such as toluene, chloroform, methyl isobutyl ketone, dichloromethane, etc., in addition to the buffer solution. Use of such organic solvent allows advantageous proceeding of the asymmetric hydrolysis.

The reaction for producing optically active benzene derivatives (VII) from optical active alcohols (V) (step 4) comprises reacting optical active alcohols (V) with an alkylating reagent or an acylating reagent (VI).

The alkylating reagent or acylating reagent used in this reaction is selected from the halides such as chlorides, bromides and iodides or the sulfuric esters (methanesulfonic esters, ethanesulfonic esters, benzene sulfonic esters, toluenesulfonic esters, etc.), or aliphatic carboxylic acids or their derivatives, viz. aliphatic carboxylic acid anhydrides or aliphatic carboxylic acid halides ("halides" signifying chlorides, bromides and iodides), all having an alkoxyalkyl moiety of 1 to 20 carbon atoms or an alkyl moiety of 1 to 20 carbon atoms which may be substituted with a halogen atom. Examples of these alkyl and alkoxy moieties include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, 1-methylethyl, 2-methylbutyl, 2,3-dimethylbutyl, 2,3,3-trimethylbutyl, 2-methylpentyl, 3-methylpentyl, 2,3-dimethylpentyl, 2,4-dimethylpentyl, 2,3,3,4-tetramethylpentyl, 2-methylhexyl, 3-methylhexyl, 4-methylhexyl, 2,5-dimethylhexyl, 2-methylheptyl, 2-methyloctyl, 2-trihalomethylpentyl, 2-trihalomethylhexyl, 2-trihalomethylheptyl, 2-halopropyl, 3-halo-2-methylpropyl, 2,3-dihalopropyl, 2-halobutyl, 3-halobutyl, 2,3-dihalobutyl, 2,4-dihalobutyl, 3,4-dihalobutyl, 2-halo-3-methylbutyl, 2-halo-3,3-dimethylbotyl, 2-halopentyl, 3-halopentyl, 4-halopentyl, 2,4-dihalopentyl, 2,5-dihalopentyl, 2-halo-3-methylpentyl, 2-halo-4-methylpentyl, 2-halo-3-monohalomethyl-4-methylpentyl, 2-halohexyl, 3-halohexyl, 4-halohexyl, 5-halohexyl, 2-haloheptyl, 2-halooctyl ("halo" in the above alkyl groups signifying fluorine, chlorine, bromine or iodine), methoxymethyl, methoxyethyl, methoxypropyl, methoxybutyl, methoxypentyl, methoxyhexyl, methoxyheptyl, methoxyoctyl, methoxynonyl, methoxydecyl, ethoxymethyl, ethoxyethyl, ethoxypropyl, ethoxybutyl, ethoxypentyl, ethoxyhexyl, ethoxyheptyl, ethoxyoctyl, ethoxynonyl, ethoxydecyl, propoxymethyl, propoxyethyl, propoxypropyl, propoxybutyl, propoxypentyl, propoxyhexyl, propoxyoctyl, propoxydecyl, butoxymethyl, butoxyethyl, butoxypropyl, butoxybutyl, butoxypentyl, butoxyhexyl, butoxyheptyl, butoxynonyl, pentyloxymethyl, pentyloxyethyl, pentyloxypropyl, pentyloxybutyl, pentyloxypentyl, pentyloxyoctyl, pentyloxydecyl, hexyloxymethyl, hexyloxyethyl, hexyloxypropyl, hexyloxybutyl, hexyloxypentyl, hexyloxyhexyl, hexyloxyoctyl, hexyloxynonyl, hexyloxydecyl, heptyloxymethyl, heptyloxyethyl, heptyloxypropyl, heptyloxypentyl, octyloxymethyl, octyloxyethyl, decyloxymethyl, decyloxyethyl, and decyloxypropyl.

Said alkoxyalkyl moiety of 1 to 20 carbon atoms or said alkyl moiety of 1 to 20 carbon atoms which may be substituted with a halogen atom may be optical active groups.

Some of the optically active carboxylic acids having said optical active groups can be obtained by oxidizing the corresponding alcohols or by reductive deamination of amino acids. Some of them exist in nature or can be derived from optically active amino acids or oxyacids such as mentioned below which can be obtained by resolution: alanine, varine, leucine, isoleucine, phenylalanine, serine, threonine, allothreonine, homoserine, alloisoleucine, tert-leucine, 2-amino acid, norvaline, ornithine, lysine, hydroxylysine, phenylglycine, trifluoroalanine, aspartic acid, glutamic acid, lactic acid, mandelic acid, tropic acid, 3-hydroxybutyric acid, malic acid, tartaric acid, osopropylmalic acid, etc.

The alkylating reagent or acylating reagent of the formula (VI) can be used in any amount not less than one equivalent to the optically active alcohol (V), but usually it is used in an amount range of 1 to 5 equivalents to said alcohol (V).

The reaction of optically active alcohols and alkylating agent is carried out in the presence or absence of a solvent. As the solvent, there can be used, beside those mentioned above in the explanation of step 2, the polar solvents such as dimethyl sulfoxide, hexamethyl phosphorylamide, N-methylpyrrolidone, etc.

The reaction temperature is usually in the range from −50° C. to 120° C., preferably from −30° C. to 100° C.

The condensation reaction of said optical active alcohols and alkylating agent is carried out in the presence of a catalyst (a basic or acid substance).

In case the alkylating agent (VI) is an alkyl halide (a chloride, bromide or iodide having an alkoxyalkyl group of 1 to 20 carbon atoms or an alkyl group of 1 to 20 carbon atoms which may be substituted with a halogen atom. Among alkyl halides, an alkyl bromide or an alkyl iodide is preferably used) or a sulfuric ester, there can be used, as catalyst (basic substance), alkali metal hydrides such as sodium hydride and potassium hydride, alkali metals such as lithium, sodium and potassium, alkali metal alcoholates such as sodium ethylate and sodium methylate, alkali metal carbonates such as sodium carbonate and potassium carbonate, alkali metal amides such as lithium diisopropyl amide and lithium bis(trimethylsilyl)amide, butyl lithium and the like.

Such catalyst (basic substance) needs to be used in an amount not less than one equivalent to the optical active alcohol. The upper shreshold amount is not defined, but the preferred amount range of the catalyst is 1 to 5 equivalents to said alcohol.

In case of using an acid anhydride or acid halide of said aliphatic carboxylic acids as acylating reagent (VI) (the amount thereof used being preferably 1 to 4 equivalents to the optical active alcohol (V)), there can be used, as catalyst (basic substance), organic or inorganic basic materials such as dimethylaminopyridine, triethylamine, tri-n-butylamine, pyridine, picoline, collidine, imidazole, sodium carbonate, sodium methylate, potassium hydrogencarbonate and the like.

Organic or inorganic acids such as toluenesulfonic acid, methanesulfonic acid, sulfuric acid, etc., are also usable as catalyst (acid substance). Especially when an acid halide of aliphatic carboxylic acids is used as alkylating agent, pyridine and triethylamine are most preferably used as catalyst (basic substance).

The amount of such catalyst (either basic or acid substance) used in the reaction is not necessarily specified as it differs depending on the type of the acid anhydride or acid halide of aliphatic carboxylic acid used and its combination with the catalyst (basic or acid substance), but in case of using an acid halide as an acylating reagent, the catalyst is used in an amount not less than one equivalent to such acid halide.

When an aliphatic carboxylic acid is used as acylating reagent (VI), dehydrating-condensation is carried out by using said carboxylic acid in an amount of usually 1 to 2 equivalents to the optical active alcohol (V) in the presence of a condensing agent to produce an optically active benzene derivative (VII).

Carbodiimides such as N,N'-dicyclohexylcarbodiimide, N-cyclohexyl-N'-(4-diethylamino)cyclohexylcarbodiimide, etc., are preferably used as condensing agent, and if necessary an organic base such as 4-pyrrolidinopyridine, pyridine, triethylamine and the like is used concurrently.

The condensing agent is used usually in an amount of 1 to 1.2 equivalent to the aliphatic carboxylic acid. In case of using an organic base concurrently, the amount thereof used is 0.01 to 0.2 equivalent to said condensing agent.

In the reaction of said optical active alcohol (V) and alkylating reagent or acylating reagent (VI), the reaction time is not specified; the moment when the optical active alcohol compound used as starting material has vanished may be taken as the end point of the reaction.

The reaction mixture is subjected to the ordinary separating operations such as extraction, separation of liquid phase, concentration, etc., whereby an optically active benzene derivative (VII) can be obtained in a high yield. If necessary, the product may be purified by column chromatography, recrystallization or other means, but the reaction mixture can be subjected immediately to the treatment of the next step.

The reaction for producing the objective optically active aromatic carboxylic acid derivatives from said optically active benzene derivatives (VII) (step 5) usually comprises hydrolysis or catalytic hydrogenation of optically active benzene derivatives. Here, in case the optically active benzene derivative (VII) used in this reaction is of the ester type (m=1 in the formula (VII)), not only $R_1$ but also

under-goes the hydrolysis reaction simultaneously, so that the hydrolysis reaction (under an alkaline condition) is applied only when the benzene derivative (VII) is of the ether type (m=0).

The alkalis usable in this hydrolysis reaction include alkali metal hydroxides such as sodium hydroxide and potassium hydroxide, alkali metal (hydrogen)carbonates and alkali metal carbonates such as sodium hydrogencarbonate, potassium hydrogencarbonate, sodium carbonate and potassium carbonate, and alkali earth metal hydroxides such as calcium hydroxide, etc. Such alkali is preferably used as an aqueous solution. The amount of such alkali used needs to be not less than one equivalent to the optically active benzene derivative (VII), usually in the range of 1 to 10 equivalents to said benzene derivative (VII).

In this reaction, water is required to be present in an amount not less than one equivalent to the optically active benzene derivative (VII). This reaction is usually carried out in the presence of an excess amount of water, but if necessary an organic solvent (water-soluble organic solvent such as methanol, ethanol, tetrahydrofuran, etc.) may be allowed to coexist.

The reaction temperature is usually in the range of $-20°$ C. to $100°$ C. The reaction time is not specified.

After the reaction has been completed, the organic solvent is eliminated from the reaction mixture if such is necessary and the substances dissolved in the concentrated residue or in the reaction mixture are separated out by adding an acid and subjected to such treatments as extraction, concentration, etc., to obtain the objective optically active aromatic carboxylic acid derivative (m=0 in the formula (I)).

The debenzylation reaction for obtaining said derivatives of the formula (I) by catalytic hydrogenation is applied when $R_1$ in the starting material (VII) is

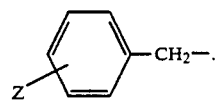

In this case, m may be 0 or 1.

Palladium type metal catalysts, such as palladium-carbon, palladium oxide, palladium black, palladium chloride, etc., are preferably used as hydrogenation catalyst in the above reaction. Nickel type catalysts such as Raney nickel, nickel-diatomaceous earth, etc., are also usable as hydrogenation catalyst.

The amount of such catalyst used is usually in the range of 0.001 to 0.5 parts by weight, preferably 0.005 to 0.3 parts by weight, based on the optically active benzene derivative.

The reaction is usually carried out in a solvent. The solvent used in this reaction must be selected from those inert to the reaction, for example, aliphatic or aromatic hydrocarbons, alcohols, ethers, ketones, esters, halogenated hydrocarbons, aprotic polar solvents and the like, such as water, dioxane, tetrahydrofuran, methanol, ethanol, n-propyl alcohol, acetone, dimethylformamide, hexane, toluene, dichloromethane, ethyl acetate, etc. These solvents may be used either singly or in combination.

This reaction is carried out under normal or raised hydrogen pressure, and preferably the moment when the hydrogen absorption has reached 1 to 12. equivalent to the optically active benzene derivative (VII) is regarded as the end point of the reaction.

The reaction temperature is in the range of $-10°$ C. to $100°$ C., preferably $10°$ C., to $60°$ C.

After the reaction, the catalyst is removed from the reaction mixture by proper means such as filtration and the residue is properly treated (concentration, etc.) to obtain the objective optically active aromatic carboxylic acid derivative (I). If necessary the product may be purified by recrystallization or column chromatography.

As described above, according to the process of this invention, it is possible to produce industrially advantageously the optically active aromatic carboxylic acid derivatives represented by the formula (I), which are the novel compounds. Further, the compounds provided according to this invention are not only useful as a liquid crystal material but can be also utilized as an intermediate for the preparation of pharmaceuticals, agricultural chemicals and such.

DESCRIPTION OF THE PREFERRED EMBODIMENTS

The present invention will be further described below in accordance with the examples thereof.

EXAMPLE 1

71.2 g (0.4 mol) of methyl 4-acetylbenzoate, 300 ml tetrahydrofuran and 100 ml of ethanol were supplied into a four-necked flask equipped with a stirrer and a thermometer. Then 7.6 g (0.2 mol) of sodium boron hydride was added at $15°-25°$ C. over a period of 3 hours. The mixture was maintained at the same temperature for 5 hours and the resulting reaction solution was poured into ice-water and extracted twice with 400 ml of ethyl acetate. The organic layer was concentrated under reduced pressure to obtain 71.0 g of methyl 4-(1-hydroxyethyl)benzoate (IIII-1) in a 98.6% yield.

70.0 g (0.388 mol) of III-1 was dissolved in a mixed solution of 300 ml of toluene and 100 ml of pyridine, followed by addition of 36.6 g (0.466 mol) of acetyl chloride at $15°-20°$ C. over a period of 2 hours. The mixture was maintained at the same temperature for one hour and then at $40°-50°$ C. for 2 hours, and the resulting reaction mixture was cooled below $10°$ C. and added with 600 ml of water. After separating the liquid phase, the organic layer was washed with a 2N hydrochloric acid solution, water, 5% sodium carbonate and water successively in that order. It was then concentrated under reduced pressure and the residue was further purified by column chromatography to give 85.2 g (99% yield) of methyl 4-(1-acetoxyethyl)benzoate (IV-1).

72.0 g (0.324 mol) of IV-1 was mixed with 400 ml of a 0.3M phosphate buffer (pH 7.5) and 4.8 g of Amano Lipase P and stirred vigorously at $40°-45°$ C. for 40 hours. The resulting reaction mixture was extracted with 600 ml of methyl isobutyl ketone.

The organic layer was concentrated under reduced pressure and the residue was purified by column chromatography using a 12:1 mixed solution of hexane and ethyl acetate as an eluting solvent to obtain 25.52 g of (+)-methyl 4-(1-hydroxyethyl)benzoate (V-1) ($[\alpha]_D^{20} = +42.3°$ (c=1, CHCl$_3$), 99.4% ee, m.p.=$52°-53°$ C.) and 39.6 g of unreacted ester.

3.6 g (0.02 mol) of V-1 was dissolved in 30 ml of dimethylformamide and cooled to $10°$ C. Then 0.62 g (0.026 mol) of sodium hydride was added and the mixture was maintained at $30°-35°$ C. for one hour. Then the solution was further added with 6.0 g (0.028 mol) of n-propyl tosylate at $20°-25°$ C. and reacted at $40°$ C. for 5 hours. The reaction mixture was poured into ice-water and extracted with 50 ml of ethyl acetate. The organic layer was washed with water and concentrated under reduced pressure, and the concentrated residue was purified by column chromatography to obtain 4.0 g (90% yield) of (+)-methyl 4-(1-propoxyethyl)benzoate (VII-1). ($[\alpha]_D^{20} = +63.4°$ (c=1, CHCl$_3$), n$_D^{20}$=1.4928).

3.33 g (0.015 mol) of VII-1 was mixed with 10 ml of methanol and 12 g of a 10% sodium hydroxide solution and stirred at room temperature for 3 hours. After the reaction, methanol was distilled off and the residue was made weakly acid with a 5% hydrochloric acid solution and extracted with 30 ml of ethyl acetate. The organic layer was concentrated under reduced pressure and the residue was purified by column chromatography using a 1:10 mixed solution of acetic acid and toluene as developing solvent to give 2.90 g (93% yield) of (+)-4-(1-propoxyethyl)benzoic acid (I-1). ($[\alpha]_D^{20} = +64.3°$ (c=1, CHCl$_3$), m.p.=$56°-58°$ C.).

EXAMPLE 2

A solution of 3.6 g. (0.02 mol) of V-1 obtained in Example 1 in 30 ml of N-methylpyrrolidone was cooled to $5°$ C., followed by addition of 0.95 g (0.04 mol) of sodium hydride. The mixture was maintained at $30°-35°$ C. for one hour, then added with 7.1 g (0.05 mol) of methyl iodide at $15°-20°$ C. and reacted at $20°-30°$ C. for 2 hours and further at $40°-50°$ C. for additional 2 hours. The resulting reaction mixture was poured into ice-water and extracted with 60 ml of ethyl acetate. The extract was further treated according to Example 1 to obtain 3.59 g (92.5% yield) of (+)-methyl 4-(1-methoxyethyl)benzoate (VII-2). ($[\alpha]_D^{20} = +75.9°$ (c=1, CHCl$_3$), n$_D^{20}$=1.4996).

2.91 g (0.015 mol) of VII-2 was mixed with 10 ml of tetrahydrofuran and 9.35 g (0.025 mol) of 15% potassium hydroxide and stirred at room temperature for 3 hours. After the reaction, tetrahydrofuran was distilled away.

The residue was made weakly acid with 1N sulfuric acid and extracted with 30 ml of ethyl acetate. The organic layer was concentrated under reduced pressure and the residue was further treated according to Example 1 to obtain 2.49 g (92% yield) of (+)-4-(1-methoxyethyl)benzoic acid (I-2). ($[\alpha]_D^{20} = +92.5°$ (c=1, CHCl$_3$), m.p.=$99°-102°$ C.).

EXAMPLE 3

A solution consisting of 3.6 g (0.02 mol) of V-1 obtained in Example 1 and 30 ml of dimethylformamide was cooled to $10°$ C., then added with 0.62 g (0.026 mol) of sodium hydride and kept at $30°-35°$ C. for one hour. The mixture was further added with 7.69 g (0.03 mol) of n-hexyl tosylate at $20°-25°$ C. and reacted at $40°-50°$ C. for 5 hours. The reaction mixture was treated according to Example 1 to obtain 4.60 g (92% yield) of (+)-methyl 4-(1-hexyloxyethyl)benzoate (VII-3). ($[\alpha]_D^{20}=+60.6°$ (c=1, CHCl$_3$), n$_D^{20}$=1.4922).

3.95 g (0.015 mol) of VII-3 was mixed with 10 ml of methanol and 12 g of a 10% sodium hydroxide solution and stirred at room temperature for 3 hours. After the reaction, methanol was distilled off and the residue was made weakly acid with a 5% HCl solution and extracted with 40 ml of ethyl acetate. The organic layer was concentrated under reduced pressure and the residue was purified by column chromatography in the manner of Example 1 to obtain 3.34 g (84% yield) of (+)-4-(1-hexyloxyethyl)benzoic acid (I-3). ($[\alpha]_D^{20}=+65.4°$ (c=1, CHCl$_3$), n$_D^{20}$=1.5056).

EXAMPLE 4

3.6 g (0.02 mol) of V-1 obtained in Example 1 was dissolved in a solution of 20 ml of dimethylformamide and 10 ml of tetrahydrofuran and cooled to 10° C. Then 0.62 g (0.026 mol) of sodium hydride was added and the mixture was maintained at 30°-35° C. for one hour.

This mixture was further added with 8.26 g (0.032 mol) of ω-ethoxypropyl tosylate and reacted at 50°-60° C. for 5 hours. The reaction mixture was treated according to Example 1 to give 4.79 g (90% yield) of (+)-methyl 4-(1-ω-ethoxypropoxyethyl)benzoate (VII-4). ($[\alpha]_D^{20}=+46.5°$ (c=1, CHCl$_3$), n$_D^{20}$=1.4933).

3.99 g (0.015 mol) of VII-4 was mixed with 24 g of a 5% sodium hydroxide solution and stirred at room temperature for 15 hours. The reaction mixture was made weakly acid with a 10% HCl solution and extracted twice with 40 ml of ethyl acetate. The organic layer was concentrated under reduced pressure and the residue was purified by column chromatography as in Example 1 to obtain 3.29 g (87% yield) of (+)-4-(1-(ω-ethoxypropoxy)ethyl)benzoic acid (I-4). ($[\alpha]_D^{20}=+57.5°$ (c=1, CHCl$_3$), n$_D^{20}$=1.5062).

EXAMPLE 5

32.2 g (0.12 mol) of ethyl 4'-acetyl-4-biphenylcarboxylate, 150 ml of chloroform and 50 ml of ethanol were supplied into a four-necked flask provided with a stirrer and a thermometer. Then 2.3 g (0.06 mol) of sodium boron hydride was added at 15°-25° C. over a period of 10 minutes. The mixture was maintained at the same temperature for 2 hours and the resulting reaction solution was poured into ice-water and extracted twice with 200 ml of ethyl acetate. The organic layer was washed with water and concentrated under reduced pressure to form 30.8 g (95% yield) of ethyl 4'-(1-hydroxyethyl)-4-biphenylcarboxylate (III-5).

29.7 g (0.11 mol) of III-5 was dissolved in a mixed solution of 150 ml of toluene and 50 ml of pyridine, and then 9.42 g (0.12 mol) of acetyl chloride was added thereto at 15°-20° C. over a period of 2 hours, and maintained at a temperature of 40°-50° C. for additional 2 hours. The reaction mixture was cooled below 10° C. and added with 300 ml of 3N hydrochloric acid. After separating the liquid phase, the organic layer was washed with water, a 5% sodium hydrogencarbonate solution and water in this order successively and then concentrated under reduced pressure, and the residue was purified by column chromatography to obtain 33.7 g (98% yield) of ethyl 4'-(1-acetoxyethyl)-4-biphenylcarboxylate (IV-5).

20.0 g (64 mmol) of IV-5 was mixed with 400 ml of 0.1M phosphate buffer (pH 7.5) and 4 g of Amano Lipase P and stirred vigorously at 40°-45° C. for 20 hours. The reaction mixture was extracted with 600 ml of methyl isobutyl ketone.

The organic layer was concentrated under reduced pressure and the residue was purified by column chromatography by using a 12:1 mixed solution of hexane and ethyl acetate as an eluting solvent to obtain 7.0 g of (+)-ethyl 4'-(1-hydroxyethyl)-4-biphenylcarboxylate (V-5) ($[\alpha]_D^{20}=+35.5°$ (c=0.544, CHCl$_3$), 98.1% ee, m.p.=74.6° C.) and 10.8 g of unreacted ester.

1.0 g (3.7 mmol) of V-5 was dissolved in 30 ml of dimethylformamide and cooled to 10° C. Then 0.19 g (4.8 mmol) of sodium hydride was added and the mixture was maintained at 30°-35° C. for one hour. Then the mixture was further added with 1.0 g (4.8 mmol) of n-propyl tosylate at 20°-25° C. and reacted at 40° C. for 5 hours. The reaction mixture was poured into ice-water and extracted with 50 ml of ethyl acetate. The organic layer was washed with water and concentrated under reduced pressure. The concentrated residue was purified by column chromatography to give 0.87 g (75% yield) of (+)-ethyl 4'-(1-propoxyethyl)-4-biphenylcarboxylate (VII-5). ($[\alpha]_D^{20}=+78.1°$ (c=0.98, CHCl$_3$)).

0.80 g (3.2 mmol) of VII-5 was mixed with 10 ml of methanol and 10 g of a 10% sodium hydroxide solution and stirred at room temperature for 3 hours. After the reaction, methanol was distilled off and the residue was made weakly acid with a 5% hydrochloric acid solution and extracted with 30 ml of ethyl acetate. The organic layer was concentrated under reduced pressure and the residue was purified by column chromatography using a 1:10 mixed solution of acetic acid and toluene as eluting solvent to obtain 0.70 g (96% yield) of (+)-4'-(1-propoxyethyl)-4-biphenylcarboxylic acid (I-5). ($[\alpha]_D^{20}=+84.2°$ (c=0.82, CHCl$_3$), m.p.=191.2° C.).

EXAMPLE 6

A solution of 1.0 g (3.7 mmol) of V-5 obtained in Example 5 and 30 ml of N-metnylpyrrolidone was cooled to 5° C., followed by addition of 0.19 g (4.8 mmol) of sodium hydride. The mixture was maintained at 30°-35° C. for one hour, then added with 1.23 g (4.8 mmol) of hexyl tosylate at 15°-20° C. and reacted at 20°-30° C. for 2 hours and further at 40°-50° C. for additional 2 hours. The reaction mixture was poured into ice-water and extracted with 60 ml of ethyl acetate. The extract was further treated according to Example 5 to obtain 1.09 g (83% yield) of (+)-ethyl 4'-(1-hexyloxyethyl)-4-biphenylcarboxylate (VII-6). ($[\alpha]_D^{20}=+64.5°$ (c=1.01, CHCl$_3$)).

1.00 g (2.8 mmol) of VII-6 was mixed with 10 ml of tetrahydrofuran and 10 g of 10% potassium hydroxide and stirred at room temperature for 3 hours. After the reaction, tetrahydrofuran was distilled off.

The residue was made weakly acid with 1N sulfuric acid and extracted with 30 ml of ethyl acetate. The organic layer was concentrated under reduced pressure and the residue was treated according to Example 5 to obtain 0.90 g (98% yield) of (+)-4'-(1-hexyloxyethyl)-4-biphenylcarboxylic acid (I-6). ($[\alpha]_D^{20}=+71.8°$ (c=0.309, CHCl$_3$), m.p.=154.1° C.).

EXAMPLE 7

A solution composed of 1.0 g (3.7 mmol) of V-5 obtained in Example 5 and 30 ml of dimethylformamide was cooled to 10° C., followed by addition of 0.19 g (4.8 mmol) of sodium hydride and standing at 30°-35° C. for one hour. Then the mixture was added with 1.63 g (4.8 mmol) of n-dodecyl tosylate at 20°-25° C. and reacted at 40°-50° C. for 5 hours. The reaction mixture was further treated in accordance with Example 5 to obtain 1.31 g (81% yield) of (+)-ethyl 4'-(1-dodecyloxyethyl)-4-biphenylcarboxylate (VII-7). ($[\alpha]_D^{20} = +46.0°$ (c=0.99, CHCl$_3$)).

1.0 g (2.28 mmol) of VII-7 was mixed with 10 ml of methanol and 12 g of a 10% sodium hydroxide solution and stirred at room temperature for 3 hours. After the reaction, methanol was distilled off and the residue was made weakly acid with 5% HCl and extracted with 40 ml of ethyl acetate. The organic layer was concentrated under reduced pressure and the residue was purified by column chromatography in the manner of Example 5 to obtain 0.92 g (98% yield) of (+)-4'-(1-dodecyloxyethyl)-4-biphenylcarboxylic acid (I-7). ($[\alpha]_D^{20} = +51.7°$ (c=0.73, CHCl$_3$), m.p.=70.5° C.).

EXAMPLE 8

1.0 g (3.7 mmol) of V-5 obtained in Example 5 was dissolved in a mixed solution of 20 ml of dimethylformamide and 10 ml of tetrahydrofuran and cooled to 10° C. Then 0.19 g (4.8 mmol) of sodium hydride was added and the mixture was maintained at 30°-35° C. for one hour.

This mixture was further added with 1.24 g (4.8 mmol) of ω-ethoxypropyl tosylate and reacted at 50°-60° C. for 5 hours, and the reaction mixture was further treated according to Example 5 to obtain 0.95 g (72% yield) of (+)-ethyl 4'-(1-ethoxypropoxyethyl)-4-biphenylcarboxylate (VII-8). ($[\alpha]_D^{20} = +65.5°$ (c=0.978, CHCl$_3$)).

0.71 g (2 mmol) of VII-8 was mixed with 24 g of a 5% sodium hydroxide solution and stirred at room temperature for 15 hours. The reaction mixture was made weakly acid with 10% HCl and extracted twice with 40 ml of ethyl acetate. The organic layer was concentrated under reduced pressure and the residue was purified by column chromatography according to Example 5 to obtain 0.63 g (96% yield) of (+)-4'-(1-(ω-ethoxypropoxy)ethyl)-4-biphenylcarboxylic acid (I-8). ($[\alpha]_D^{20} = +72.3°$ (c=0.97, CHCl$_3$)).

EXAMPLE 9

30.49 g (0.12 mol) of benzyl 4-acetylbenzoate, 50 ml of ethanol and 150 ml of chloroform were supplied into a four-necked flask provided with a stirrer and a thermometer. Then 2.3 g (0.06 mol) of sodium borohydride was added at 15°-25° C. over a period of 10 minutes, and the mixture was maintained at the same temperature for 2 hours.

The reaction mixture was poured into ice-water and extracted twice with 200 ml of ethyl acetate. The organic layer was washed with water and concentrated under reduced pressure to obtain 29.2 g (95% yield) of benzyl 4-(1-hydroxyethyl)benzoate (III-9). $n_D^{25} = +1.5680$.

27.95 g (0.11 mol) of III-9 was dissolved in a mixed solution of 150 ml of toluene and 50 ml of pyridine, followed by addition of 9.42 g (0.12 mol) of acetyl chloride at 15°-20° C. over a period of 2 hours and standing at the same temperature for one hour and then at 30°-35° C. for 2 hours. The reaction mixture was cooled below 10° C. and added with 300 ml of a 3N hydrochloric acid solution. After the organic layer was separated, the organic layer was washed with water, a 5% sodium bicarbonate solution and water successively in that order, then concentrated under reduced pressure and purified by column chromatography to obtain 32.14 g (98% yield) of benzyl 4-(1-acetoxyethyl)benzoate (IV-9).

19.08 g (64 mmol) of IV-9 was mixed with 400 ml of 0.1M phosphate buffer (pH 7.0), 10 ml of chloroform and 4 g of Amano Lipase P and stirred vigorously at 40°-45° C. for 20 hours. The reaction mixture was extracted with 600 ml of methyl isobutyl ketone. The organic layer was concentrated under reduced pressure and the residue was purified by column chromatography using a 12:1 mixed solution of hexane and ethyl acetate as eluting solvent to obtain 7.21 g of (+)-benzyl 4-(1-hydroxyethyl)benzoate (V-9). ($[\alpha]_D^{25} = +35.4°$ (c=1, CHCl$_3$, $n_D^{25} = 1.5691$).

1.28 g (5 mmol) of V-9 was dissolved in 15 ml of dimethyl formamide and cooled to 10° C. To this solution was added 0.15 g (6 mmol) of sodium hydride. After standing at 30°-35° C. for one hour, the mixture was further added with 2.1 g (6 mmol) of n-dodecyl tosylate and reacted at 40° C. for 5 hours. The reaction mixture was poured into ice-water and extracted with 50 ml of ethyl acetate. The organic layer was washed with water and concentrated under reduced pressure, and the residue was purified by column chromatography to obtain 1.74 g (82% yield) of (+)-benzyl 4-(1-dodecyloxyethyl)benzoate (VII-9). $n_D^{25} = 1.5016$, $[\alpha]_D^{25} = +32.4°$ (c=1, CHCl$_3$).

1 g (2.5 mmol) of VII-9, 0.2 g of 5% Pd-carbon (50% wet), 10 ml of methanol and 5 ml of ethyl acetate were mixed and hydrogenated under normal pressure. When the hydrogen absorption reached 60 ml, the reaction was stopped and the catalyst was filtered away. The filtrate was concentrated and the residue was purified by column chromatography using a 20:1 mixture of toluene and acetic acid as an eluting solvent to obtain 0.72 g of (+)-4-(1-dodecyloxyethyl)benzoic acid (I-9). $[\alpha]_D^{25} = +32.7°$ (c=1, CHCl$_3$), m.p.=49.5°-50° C.

EXAMPLE 10

0.5 g (1.2 mmol) of VII-9 obtained in Example 9, 1.5 g of a 10% sodium hydroxide solution and 10 ml of methanol were mixed and reacted at 25°-30° C. for 5 hours. The reaction mixture was adjusted to a pH 3 with 10% hydrochloric acid and extracted with 20 ml of toluene. The organic layer was washed with water and concentrated under reduced pressure. The residue was purified by column chromatography to obtain 0.37 g of (+)-4-(1-dodecyloxyethyl)benzoic acid (I-10). M.p.=49.5°-50.5° C., $[\alpha]_D^{25} = +32.6°$ (c=1, CHCl$_3$).

EXAMPLE 11

2.56 g (0.01 mol) of V-9 obtained in Example 9 was dissolved in 20 ml of N-methylpyrrolidone and cooled to 10° C. To this solution was added 0.31 g (0.013 mol) of sodium hydride, followed by standing at 30°-35° C. for one hour. The mixture was further added with 3.6 g (0.014 mol) of n-hexyl tosylate at 20°-25° C. and reacted at 40° C. for 5 hours. The reaction mixture was poured into ice-water and extracted with 50 ml of ethyl acetate. The organic layer was washed with water and concentrated under reduced pressure, and the residue was purified by column chromatography to obtain 3.11 g (92% yield) of (+)-benzyl 4-(1-hexyloxyethyl)benzoate (VII-11).

1.69 g (5 mmol) of VII-11 was mixed with 0.1 g of 5% Pd-carbon and 15 ml of ethanol and hydrogenated under normal pressure. When the hydrogen absorption reached 120 ml, the reaction was stopped and the reaction mixture was further treated and purified according to Example 9 to obtain 1.21 g (97.5% yield) of (+)-4-(1-hexyloxyethyl)benzoic acid (I-2). $n_D^{25}=1.5040$, $[\alpha]_D^{25}=+65.4°$ (c=1, CHCl$_3$).

EXAMPLE 12

0.85 g (2.5 mmol) of VII-11 obtained in Example 11, 5 ml of tetrahydrofuran and 5 g of a 5% potassium hydroxide solution were mixed and reacted at 20° C. for 5 hours. The reaction mixture was adjusted to a pH 2 with 10% hydrochloric acid and tetrahydrofuran was distilled off under reduced pressure. The residue was extracted with 20 ml of toluene and the organic layer was washed with water and further treated and purified according to Example 10 to obtain 0.6 g (96% yield) of (+)-4-(1-hexyloxyethyl)benzoic acid (I-12). $n_D^{25}=1.5038$, $[\alpha]_D^{25}=+64.4°$ (c=1, CHCl$_3$).

EXAMPLE 13

32.17 g (0.12 mol) of methylbenzyl 4-acetylbenzoate, 50 ml of ethanol, 100 ml of dichloromethane and 50 ml of tetrahydrofuran were supplied into the same flask as used in Example 9, and then 2.3 g (0.06 mol) of sodium boron hydride was added at 15°-25° C. over a period of 10 minutes. After standing at the same temperature for 2 hours, the reaction mixture was poured into ice-water and treated similarly to Example 9 to obtain 31.43 g (97% yield) of methylbenzyl 4-(1-hydroxyethyl)benzoate (III-13).

29.71 g (0.11 mol) of III-13 was dissolved in a mixed solution of 200 ml of dichloromethane and 50 ml of pyridine, followed by dropwise addition of 50 ml of a dichloromethane solution containing 9.42 g (0.12 mol) of acetyl chloride at room temperature. Approximately 2 hours later, the reaction solution was poured into 300 ml of 3N hydrochloric acid and extracted. The organic layer was washed with water, a 7% sodium bicarbonate solution and water in this order successively and then dried over anhydrous magnesium sulfate. The solvent was distilled off to give 33.3 g (97% yield) of methylbenzyl 4-(1-acetoxyethyl)benzoate (IV-13) as a light-yellow oil.

15.6 g (50 mmol) of IV-13 was mixed with 200 ml of 0.3M phosphate buffer (pH 7.0), 10 ml of chloroform and 3 g of Amano Lipase P and the mixture was stirred vigorously at 38°-40° C. for 24 hours.

The reaction mixture was extracted with 600 ml of ethyl acetate. The organic layer was concentrated under reduced pressure and the residue was purified by column chromatography using a 12:1 mixed solution of hexane and ethyl acetate as eluting solvent to obtain 5.95 g of (+)-methylbenzyl 4-(1-hydroxyethyl)benzoate (V-13). $[\alpha]_D^{20}=+36.3°$ (c=1, CHCl$_3$), $n_D^{25}=1.5688$.

1.35 g (5 mmol) of V-13 was dissolved in 15 ml of dimethylformamide and cooled to 10° C., followed by addition of 0.15 g (6 mmol) of sodium hydride and standing at 30°-35° C. for one hour. Then the mixture was further added with 1.55 g (6 mmol) of -ethoxypropyl tosylate and reacted at 35°-40° C. for 5 hours. The reaction mixture was further treated and purified according to Example 9 to obtain 1.37 g (77% yield) of (+)-methylbenzyl 4-(1ω-ethoxypropoxyethyl)benzoate (VI-13).

0.89 g (2.5 mmol) of VI-13 was mixed with 0.1 g of 5% Pd-C and 10 ml of methanol and the mixture was subjected to catalytic hydrogenation under normal pressure. When the hydrogen absorption reached 60 ml, the reaction was stopped and the reaction mixture was further treated and purified according to Example 9 to obtain 0.61 g (97% yield) of (+)-4-(1-(ω-ethoxypropoxy)ethyl)benzoic acid (I-13). $n_D^{25}=1.5077$, $[\alpha]_D^{25}=+59.7°$ (c=1, CHCl$_3$).

EXAMPLE 14

The procedure of Example 13 was followed on the same molar scale except that 34.09 g (0.12 mol) of methoxybenzyl 4-acetylbenzoate was used in place of methylbenzyl 4-acetylbenzoate to obtain the following intermediates:

Methoxybenzyl 4-(1-hydroxyethyl)benzoate (III-14). 95.5% yield.
Methoxybenzyl 4-(1-acetoxyethyl)benzoate (IV-14). 98.5% yield.
(+)-Methoxybenzyl 4-(1-hydroxyethyl)benzoate (V-14). 2.34 g. $[\alpha]_D^{25}=+37.2°$ (c=1, CHCl$_3$), $n_D^{25}=1.5721$.

1.43 g (5 mmol) of V-14 was dissolved in 15 ml of dimethylformamide and cooled to 10° C. To this solution was added 0.15 g (6 mmol) of sodium hydride, followed by standing at 30°-35° C. for one hour. Then the mixture was further added with 2.1 g (15 mmol) of methyl iodide at 20°-25° C. and reacted at the same temperature for 3 hours and then at 40° C. for another 3 hours. The reaction mixture was further treated and purified according to Example 9 to obtain 1.36 g (91% yield) of (+)-methoxybenzyl 4-(1-methoxyethyl)benzoate (VII-14).

0.75 g (2.5 mmol) of VII-14, 0.03 g of palladium oxide and 10 ml of methanol were mixed and subjected to catalytic hydrogenation under normal pressure. When the hydrogen absorption reached 63 ml, the reaction was stopped and the reaction mixture was subjected to the same treatments and purification as in Example 9 to obtain 0.43 g (95% yield) of (+)-4-(1-methoxyethyl)benzoic acid (I-14). M.p.=99°-100° C., $[\alpha]_D^{25}=+94.2°$ (c=1, CHCl$_3$).

EXAMPLE 15

33.0 g (0.1 mol) of benzyl 4'-acetyl-4-biphenylcarboxylate, 200 ml of tetrahydrofuran and 50 ml of ethanol were supplied into the same flask as used in Example 9. Then 3.8 g (0.1 mol) of sodium borohydride was added at 15°-25° C. over a period of 10 minutes. After standing at the same temperature for 2 hours, the reaction solution was poured into ice-water and extracted twice with 300 ml of chloroform. The organic layer was washed with water and concentrated under reduced pressure to obtain 32.9 g (99% yield) of benzyl 4'-(1-hydroxyethyl)-4-biphenylcarboxylate (III-15).

29.9 g (0.09 mol) of III-15 was dissolved in a mixed solution of 150 ml of toluene and 50 ml of pyridine, followed by addition of 9.42 g (0.12 mol) of acetyl chloride at 15°-20° C. over a period of 2 hours. The mixture was maintained at the same temperature for 2 hours and then at 40°-45° C. for another 2 hours. The reaction mixture was cooled below 10° C. and added with 300 ml of 3N hydrochloric acid. After separating the liquid phase, the organic layer was washed with water, 5% sodium hydrogencarbonate and water successively in that order and concentrated under reduced pressure. The residue was purified by column chromatography to give 33.0 g (98% yield) of benzyl 4'-(1-acetoxyethyl)-4-biphenylcarboxylate (IV-15).

29.9 g (0.08 mol) of IV-15 was mixed with 800 ml of 0.1M phosphate buffer (pH 7.5), 30 ml of chloroform and 6 g of Amano Lipase P and the mixture was stirred vigorously at 30°–35° C. for 20 hours. The reaction mixture was extracted with 600 ml of methyl isobutyl ketone. The organic layer was concentrated under reduced pressure and the residue was purified by column chromatography using a 12:1 mixed solution of chloroform and ethyl acetate as eluting solvent to obtain 10.6 g of (+)-benzyl 4'-(1-hydroxyethyl)-4-biphenylcarboxylate (V-15). $[\alpha]_D^{25} = +23.7°$ (c=1, CHCl$_3$), m.p.=104°–106° C.

1.66 g (5 mmol) of V-15 was dissolved in 20 ml of dimethylformamide and cooled to 10° C., followed by addition of 0.15 g (6 mmol) of sodium hydride and standing at 30°–35° C. for one hour. Then the mixture was further added with 1.7 g (6 mmol) of n-octyl tosylate at 20°–25° C. and reacted at 40° C. for 5 hours. The reaction mixture was poured into ice-water and extracted with 50 ml of chloroform. The organic layer was washed with water and concentrated under reduced pressure, and the residue was purified by column chromatography to obtain 1.49 g (81% yield) of (+)-benzyl 4'-(1-octyloxyethyl)-4-biphenylcarboxylate (VII-15). $[\alpha]_D^{20} = +26.2°$ (c=1, CHCl$_3$).

1.03 g (2.8 mmol) of VII-15, 0.1 g of 5% Pd-C, 15 ml of tetrahydrofuran and 5 ml of methanol were mixed and the mixture was subjected to catalytic hydrogenation under normal pressure. When the hydrogen absorption reached 66 ml, the reaction was stopped and the catalyst was filtered away. The filtrate was concentrated and purified by column chromatography to obtain 0.76 g (98% yield) of (+)-4'-(1-octyloxyethyl)-4-biphenylcarboxylic acid. $[\alpha]_D^{25} = +67.5°$ (c=1, CHCl$_3$), m.p.=139°–140° C.

EXAMPLE 16

1.66 g (5 mmol) of V-15 obtained in Example 15 was dissolved in 20 ml of dimethylformamide and cooled to 10° C. To this solution was added 0.15 g (6 mmol) of sodium hydride, followed by standing at 30°–35° C. for 2 hours. Then the mixture was further added with 1.22 g (10 mmol) of propyl bromide at 20°–25° C. and reacted at the same temperature for 2 hours and further at 40°–50° C. for 5 hours. The reaction mixture was subjected to the same treatments and purification as in Example 15 to obtain 1.50 g (80% yield) of (+)-benzyl 4'-(1-propoxyethyl)-4-biphenylcarboxylate (VII-16).

1.05 g (2.8 mmol) of VII-16, 0.1 g of 5% Pd-C, 15 ml of tetrahydrofuran and 5 ml of methanol were mixed and hydrogenated under normal pressure. When the hydrogen absorption reached 68 ml, the reaction was stopped. The catalyst was filtered away. The filtrate was concentrated and the residue was purified by column chromatography to obtain 0.77 g (97.5% yield) of (+)-4'-(1-propoxyethyl)-4-biphenylcarboxylic acid (I-16). $[\alpha]_D^{25} = +76.9°$ (c=1, CHCl$_3$), m.p.=172°–173° C.

EXAMPLE 17

36.5 g (0.1 mol) of p-chlorobenzyl 4'-acetyl-4-biphenylcarboxylate, 150 ml of chloroform and 50 ml of ethanol were supplied into the same flask as used in Example 9. Then 3.8 g (0.1 mol) of sodium borohydride was added at 15°–25° C. over a period of 10 minutes. The mixture was kept at the same temperature for 2 hours, and the reaction solution was poured into ice-water and extracted twice with 200 ml of ethyl acetate. The organic layer was washed with water and concentrated under reduced pressure to obtain 36.5 (99.5% yield) of p-chlorobenzyl 4'-(1-hydroxyethyl)-4-biphenylcarboxylate (III-17).

33.0 g (0.09 mol) of III-17 was dissolved in a mixed solution of 150 ml of toluene and 50 ml of pyridine, followed by addition of 9.42 g (0.12 mol) of acetyl chloride at 15°–20° C. for 2 hours. The mixture was maintained at the same temperature for one hour and then at 40°–50° C. for 2 hours. The resulting reaction mixture was cooled below 10° C. and added with 300 ml of a 3N hydrochloric acid solution. After separating the liquid phase, the organic layer was washed with water, 5% sodium hydrogencarbonate and water in that order successively and then concentrated under reduced pressure. The residue was further purified by column chromatography to obtain 36.4 g (99.0% yield) of p-choorobenzyl 4'-(1-acetoxyethyl)-4-biphenyl-carboxylate (IV-17).

32.7 g (0.08 mol) of IV-17 was mixed with 800 ml of 0.1M phosphate buffer (pH 7.5), 30 ml of chloroform and 6 g of Amano Lipase P and the mixture was stirred vigorously at 40°–45° C. for 20 hours. The reaction mixture was extracted with 600 ml of methyl isobutyl ketone. The organic layer was concentrated under reduced pressure and the residue was purified by column chromatography using a 12:1 mixed solution of hexane and ethyl acetate as eluting solvent to obtain 13.8 g of (+)-p-chlorobenzyl 4'-(1-hydroxyethyl)-4-biphenylcarboxylate (V-17) ($[\alpha]_D^{20} = +21.7°$ (c=0.544, CHCl$_3$), m.p.=108°–110.5° C.) and 16.5 g of unreacted ester.

3.65 g (10 mmol) of V-17 was dissolved in 30 mo of dimethylformamide and cooled to 10° C. To this solution was added 0.48 g (12 mmol) of sodium hydride, followed by standing at 30°–35° C. for one hour. Then the mixture was further added with 5.1 g (12 mmol) of n-octadecyl tosylate at 20°–25° C. and reacted at 40° C. for 5 hours. The reaction mixture was poured into ice-water and extracted with 50 ml of ethyl acetate. The organic layer was washed with water and concentrated under reduced pressure. The residue was purified by column chromatography to obtain 5.07 g (82% yield) of (+)-p-chlorobenzyl 4'-(1-octadecyloxyethyl)-4-biphenylcarboxylate (VII-17). $[\alpha]_D^{20} = +21.1°$ (c=0.98, CHCl$_3$), $n_D^{20} = 1.5314$.

3.1 g of VII-17, 0.5 g of 5% Pd-C, 40 ml of tetrahydrofuran and 10 ml of methanol were mixed and hydrogenated under normal pressure. When the hydrogen absorption reached 120 ml, the reaction was stopped. The catalyst was filtered away and the filtrate was concentrated and column-chromatographed using chloroform/acetic acid (10/1) to obtain (+)-4'-(1-octadecyloxyethyl)-4-biphenylcarboxylic acid (I-17). $[\alpha]_D^{25} = +55.8°$ (c=1, CHCl$_3$), m.p.=145°–146° C.

EXAMPLE 18

1.28 g (5 mmol) of V-9 obtained in Example 9 was dissolved in 15 ml of dimethylformamide and cooled to 10° C., followed by addition of 0.15 g (6 mmol) of sodium hydride and standing at 30°–35° C. for one hour. Then the mixture was further added with 1.45 g (6 mmol) of s-2-methylbutyl tosylate at 20°–25° C. and reacted at 40°–50° C. for 5 hours. The reaction mixture was further treated and purified according to Example 9 to obtain 1.40 g (86% yield) of benzyl (+)-4-(1-s-2'-methylbutoxyethyl)benzoate (VII-18).

0.81 g (2.5 mmol) of VII-18, 0.2 g of 5% Pd-C and 15 ml of methanol were mixed and the mixture was reacted, treated and purified according to Example 9 to obtain 0.58 g (98% yield) of (+)-4-(1-(2-(s)-methylbutoxy)ethyl)benzoic acid (I-18). $n_D^{25}=1.4918$, $[\alpha]_D^{25}=+46.8°$ (c=1, CHCl$_3$).

EXAMPLE 19

60.98 g (0.24 mol) of benzyl 4-acetylbenzoate (II-19), 100 ml of ethanol and 300 ml of chloroform were supplied into a four-necked flask equipped with a stirrer and a thermometer. Then 4.6 g (0.12 mol) of sodium borohydride was added at 15°–25° C., over a period of 10 minutes. The mixture was kept at the same temperature for 2 hours and the resulting reaction mixture was poured into ice-water and extracted twice with 200 ml of ethyl acetate. The organic layer was washed with water and concentrated under reduced pressure to obtain 58.37 g (95% yield) of benzyl 4-(1-hydroxyethyl)-phenylcarboxylate (III-19). $n_D^{25}=1.5682$.

55.90 g (0.22 mol) of III-19 was dissolved in a mixed solution of 300 ml of toluene and 100 ml of pyridine. Then 18.84 g (0.24 mol) of acetyl chloride was added at 15°–20° C. over a period of 2 hours, and the mixture was maintained at the same temperature for one hour and further at 30°–35° C., for 2 hours. The reaction mixture was cooled below 10° C., and added with 600 ml of a 3N hydrochloric acid solution. After separating the liquid phase, the organic layer was washed with water, a 5% sodium bicarbonate solution and water successively in that order, then concentrated under reduced pressure and purified by column chromatography to obtain 63.75 g (98% yield) of benzyl 4-(1-acetoxyethyl)phenylcarboxylate (IV-19). $n_D^{25}=1.5304$.

29.81 g (0.1 mol) of IV-19 was mixed with 600 ml of 0.1M phosphate buffer (pH 7.0), 15 ml of chloroform and 6 g of Amano Lipase P, and the mixture was stirred vigorously at 40°–45° C., for 20 hours. The reaction mixture was extracted with 900 ml of methyl isobutyl ketone. The organic layer was concentrated under reduced pressure and the residue was purified by column chromatography using a 12:1 mixed solution of hexane and ethyl acetate as eluting solvent to obtain 11.21 g of (+)-benzyl 4-(1-hydroxyethyl)phenylcarboxylate (V-19) ($[\alpha]_D^{25}=+35.6°$ (c=1, CHCl$_3$), $n_D^{25}=1.5694$) and 15.96 g of (−)-benzyl 4′-(1-acetoxyethyl)-4-phenylcarboxylate ($[\alpha]_D^{25}=-52°$ (c=1, CHCl$_3$), $n_D^{25}=1.5293$).

1.02 g (4 mmol) of V-19 was dissolved in a mixed solution of 5 ml of pyridine and 10 mol of toluene, and to this solution was added dropwise 0.66 g (4.4 mmol) of hexanoyl chloride at 15°–20° C. The mixture was reacted at 20° C. for 2 hours and further at 40°–50° C. for additional 2 hours. The reaction solution was poured into ice-water and extracted with 30 ml of toluene. The toluene layer was washed with a 1N hydrochloric acid solution, a 2% sodium bicarbonate solution and water successively in that order. The organic layer was dried over anhydrous magnesium sulfate. This toluene layer was concentrated under reduced pressure and the residue was purified by silica gel column chromatography using toluene as eluting solvent to obtain 1.39 g (98% yield) of hexanoic ester of (+)-benzyl 4-(1-hydroxyethyl)phenylcarboxylate (VII-19). $[\alpha]_D^{25}=+49.2°$ (c=1, CHCl$_3$), $n_D^{25}=1.5221$.

1.06 g (3 mmol) of VII-19 was mixed with 10 ml of tetrahydrofuran and 0.1 g of 5% Pd-C and the mixture was subjected to catalytic hydrogenation in a hydrogen atmosphere under normal pressure. When the hydrogen absorption reached the molar equivalence, the reaction was stopped and the catalyst was filtered away. The filtrate was concentrated and the residue was column-chromatographed to obtain 0.75 g (95% yield) of (+)-4-(1′-hexanoyloxyethyl)benzoic acid. $[\alpha]_D^{25}=+68.8°$ (c=1, CHCl$_3$), $n_D^{25}=1.4849$.

EXAMPLE 20

10 g of (−)-benzyl 4′-(1-acetoxyethyl)-4-phenylcarboxylate obtained in Example 19, 200 ml of 0.2M phosphate buffer, 5 ml of chloroform and 1 g of Amano swine liver esterase were mixed and reacted at 30°–35° C. for 30 hours. The reaction mixture was treated and purified by following the procedure of Example 19 to obtain 7.7 g of (−)-benzyl 4-(1-hydroxyethyl)phenylcarboxylate (V-20).

1.02 g (4 mmol) of V-20 was mixed with 0.4 g (4.8 mmol) of 2(s)-methylbutanoic acid in 20 ml of dichloromethane, and to this solution were added 0.91 g (4.4 mmol) of dicyclohexylcarbodiimide and 0.02 g of 4-pyrrolidinopyridine for reacting said materials at room temperature for 12 hours. After the reaction, the precipitated crystals were filtered out and the filtrate was concentrated, the residue being chromatographed in the same way as Example 19 to obtain 1.29 g (95.0% yield) of 2(s)-methylbutanoic ester of (−)-benzyl 4-(1-hydroxyethyl)phenylcarboxylate (VII-20). $[\alpha]_D^{25}=-55.2°$ (c=1, CHCl$_3$), $n_D^{25}=1.5295$.

1.02 g (3 mmol) of VII-20 was mixed with 30 ml of ethyl acetate and 0.1 g of 2% Pd-C and the mixture was reduced under normal pressure. The resulting product was further treated and purified according to Example 19 to obtain 0.72 g (96% yield) of (−)-4-(1-(2(s)-methylbutyryloxy)ethyl)benzoic acid. $[\alpha]_D^{25}=-74°$ (c=1, CHCl$_3$), $n_D^{25}=1.5013$.

EXAMPLE 21

1.02 g (4 mmol) of V-19 obtained in Example 19, 10 ml of pyridine, 10 ml of dichloroethane and 0.76 g (4.4 mmol) of butanoic anhydride were reacted at 20°–25° C. for 15 hours. The reaction mixture was poured into ice-water and extracted with 20 ml of dichloroethane. Thereafter the same treatments and purification as in Example 19 were carried out to obtain 1.27 g (97% yield) of butanoic ester of (+)-benzyl 4-(1-hydroxyethyl)phenylcarboxylate (VII-21). $[\alpha]_D^{25}=+51.5°$ (c=1, CHCl$_3$), $n_D^{25}=1.5243$.

0.98 g (3 mmol) of VII-21 was mixed with 10 ml of tetrahydrofuran, 3 ml of ethanol and 0.05 g of palladium oxide and the mixture was reduced under normal pressure similarly to Example 19 and further treated and purified according to Example 19 to obtain 0.68 g (96% yield) of (+)-4-(1-butyryloxyethyl)benzoic acid. $[\alpha]_D^{25}=+94.2°$ (c=1, CHCl$_3$), $n_D^{25}=1.5138$.

EXAMPLE 22

32.17 g (0.12 mol) of methylbenzyl 4-acetylphenylcarboxylate, 50 ml of ethanol, 100 ml of dichloromethane and 50 ml of THF were supplied into a four-necked flask provided with a stirrer and a thermometer. Then 2.3 g (0.06 mol) of sodium borohydride was added at 15°–25° C. over a period of 10 minutes. The mixture was maintained at the same temperature for 2 hours and the reaction mixture was poured into ice-water and treated according to Example 19 to obtain 31.43 g (97% yield) of methylbenzyl 4-(1-hydroxyethyl)phenylcarboxylate (III-22).

29.71 g (0.11 mol) of III-22 was dissolved in a mixed solution of 200 ml of dichloromethane and 50 ml of pyridine, and to this solution was added dropwise 50 ml of a dichloromethane solution containing 9.42 g (0.12 mol) of acetyl chloride at room temperature. About 2 hours later, the reaction solution was poured into 300 ml of 3N hydrochloric acid and extracted therewith. The organic layer was washed with water, a 7% sodium bicarbonate solution and water in this order successively and then dried over anhydrous magnesium sulfate. The solvent was distilled off to obtain 33.3 g (97% yield) of methylbenzyl 4-(1-acetoxyethyl)phenylcarboxylate (IV-22) as a light-yellow oil.

15.6 g (50 mmol) of IV-22 was mixed with 200 ml of 0.3M phosphate buffer (pH 7.0), 10 ml of chloroform and 3 g of Amano Lipase P and the mixture was stirred vigorously at 38°–40° C. for 24 hours.

The reaction mixture was extracted with 600 ml of ethyl acetate. The organic layer was concentrated under reduced pressure and the residue was subjected to column chromatography using a 12:1 mixed solution of hexane and ethyl acetate as eluting solvent to obtain 5.95 g of methylbenzyl (+)-4-(1-hydroxyethyl)phenylcarboxylate (V-22). $[\alpha]_D^{20} = +36.3°$ (c=1, CHCl$_3$), $n_D^{25} = 1.5688$.

1.08 g (4 mmol) of V-22 was mixed in a solution of 5 ml of pyridine and 10 ml of toluene, followed by addition of 0.91 g (0.46 mmol) of decanoic acid chloride at 20° C. The mixture was stirred for 10 hours and further reacted at 40°–45° C. for 2 hours. The reaction mixture was treated and purified according to Example 19 to obtain 1.60 g (94.5% yield) of decanoic ester of (+)-methylbenzyl 4-(1-hydroxyethyl)phenylcarboxylate (VII-22). $[\alpha]_D^{25} = +44.5°$ (c=1, CHCl$_3$), $n_D^{25} = 1.5172$.

By using 1.27 g (3 mmol) of VII-22, the same operations for reduction, further treatments and purification as conducted in Example 19 were repeated to obtain (+)-4-(1-decanoyloxyethyl)benzoic acid in a 95.5% yield. $[\alpha]_D^{25} = +62°$ (c=1, CHCl$_3$), $n_D^{25} = 1.4810$.

EXAMPLE 23

The reaction procedure of Example 22 was followed except that 34.09 g (0.12 mol) of methoxybenzyl 4-acetylbenzoate was used as starting material instead of benzyl 4-acetylbenzoate. The yields of the intermediates and the objective phenylethanol derivative (V-23) were as shown below. The molar ratios of the intermediates and the starting materials used in the process were the same as in Example 22.

4-Methoxybenzyl 4-(1-hydroxyethyl)phenylcarboxylate (III-23), 96.5% yield.

4-Methoxybenzyl 4-(1-acetoxyethyl)phenylcarboxylate (IV-23), 96.3% yield.

(+)-4-Methoxybenzyl (+)-4-(1-hydroxyethyl)phenylcarboxylate (V-23), 2.34 g, $[\alpha]_D^{25} = +37°$ (c=1, CHCl$_3$), $n_D^{25} = 1.5724$.

1.14 g (4 mmol) of V-23 was added to a mixed solution of 10 ml of pyridine and 5 ml of toluene. The mixture was further added with palmitic acid chloride and reacted at 25°–30° C. for 10 hours. The reaction mixture was further treated and purified by following the procedure of Example 19 to obtain 1.91 g (90% yield) of palmitic ester of (+)-4-methoxybenzyl 4-(1-hydroxyethyl)phenylcarboxylate (VII-23). $[\alpha]_D^{25} = +36°$ (c=1, CHCl$_3$).

A mixed solution of 14.8 g (3 mmol) of VII-23 and 0.3 g of 5% Pd-C in 20 ml of ethyl acetate was hydrogenated under normal pressure. When the hydrogen absorption reached the molar equivalence, the reaction was stopped and the catalyst was filtered out. The filtrate was concentrated and the residue was columnchromatographed to obtain 1.17 g (97% yield) of (+)-4-(1-palmitoyloxyethyl)benzoic acid as a waxy solid. $[\alpha]_D^{25} = +54°$ (c=1, CHCl$_3$).

EXAMPLE 24

The procedure of Example 20 was followed except that 1.02 g (4 mmol) of (+)-benzyl 4-(1-hydroxyethyl)phenylcarboxylate (V-19) was used in place of (−)-benzyl 4-(1-hydroxyethyl)phenylcarboxylate (V-20) and that 2(s)-methylbutanoic acid (4.8 mmol) was used in place of (2s,3s)-2-chloro-3-methylphetanoic acid (VI-29) to obtain 2(s)-methylbutanoic ester of (+)-benzyl 4-(1-hydroxyethyl)phenylcarboxylate (VII-24) in a 95.5% yield. $[\alpha]_D^{25} = +67.6°$ (c=1, CHCl$_3$), $n_D^{25} = 1.5302$.

By using 1.02 g (3 mmol) of VII-24, the same operations for reaction, after-treatments and purification as in Example 19 were carried out to obtain 0.72 g (96.5% yield) of (+)-4-(1-(2(s) -methylbutyryloxy)ethyl)benzoic acid. $[\alpha]_D^{25} = +51°$ (c=1, CHCl$_3$), $n_D^{25} = 1.4821$.

EXAMPLE 25

33.0 g (0.1 mol) of benzyl 4'-acetyl-4-biphenylcarboxylate, 200 ml of tetrahydrofuran and 50 ml of ethanol were supplied into a four-necked flask provided with a stirrer and a thermometer. Then 3.8 g (0.1 mol) of sodium borohydride was added at 15°–25° C. over a period of 10 minutes. The mixture was maintained at the same temperature for 2 hours. The reaction mixture was poured into ice-water and extracted twice with 300 ml of chloroform. The organic layer was washed with water and concentrated under reduced pressure to obtain 32.9 g (99% yield) of benzyl 4'-(1-hydroxyethyl)-4-biphenylcarboxylate (III-25).

29.9 g (0.09 mol) of III-25 was dissolved in a mixed solution of 150 ml of toluene and 50 ml of pyridine, followed by addition of 9.42 g (0.12 mol) of acetyl chloride at 15°–20° C. over a period of 2 hours. The mixture was maintained at the same temperature for 2 hours and then at 40°–45° C. for another 2 hours. The reaction mixture was cooled below 10° C. and added with 300 ml of 3N hydrochloric acid. After separating the liquid phase, the organic layer was washed with water, a 5% sodium hydrogencarbonate solution and water in this order successively and concentrated under reduced pressure. The residue was further purified by column chromatography to obtain 33.0 g (98% yield) of benzyl 4'-(1-acetoxyethyl)-4-biphenylcarboxylate (IV-25).

29.9 g (0.8 mol) of IV-25 was mixed with 800 ml of 0.1M phosphate buffer (pH 7.5), 30 ml of chloroform and 6.0 g of Amano Lipase P, and the mixture was stirred vigorously at 30°–35° C. for 20 hours. The reaction mixture was extracted with 600 ml of methyl isobutyl ketone. The organic layer was concentrated under reduced pressure and the residue was subjected to column chromatography using a 12:1 mixed solution of chloroform and ethyl acetate to obtain 10.6 g of (+)-benzyl 4'-(1-hydroxyethyl)-4-biphenylcarboxylate (V-25) ($[\alpha]_D^{25} = +19.3°$ (c=1, CHCl$_3$), m.p.=108°–110.5° C.) and 17.5 g of (−)-benzyl 4'-(1-acetoxyethyl)-4-biphenylcarboxylate.

1.00 g (3 mmol) of V-25, 10 ml of pyridine, 10 ml of toluene and 0.77 g (3.6 mmol) of a hexanoic anhydride were mixed and reacted at 20°–25° C. for 15 hours. The reaction mixture was poured into ice-water and extracted with 30 ml of toluene. The organic layer was washed with a 1N hydrochloric acid solution, a 2% sodium bicarbonate solution and water in that order successively and concentrated under reduced pressure, and the residue was column-chromatographed to obtain 1.24 g (96% yield) of hexanoic ester of (+)-benzyl 4'-(1-hydroxyethyl)-4-biphenylcarboxylate (VII-25). $[\alpha]_D^{25} = +46.5°$ (c=1, CHCl₃), $n_D^{25} = 1.5480$.

0.86 g (2 mmol) of VII-25 was mixed with 30 ml of tetrahydrofuran and 0.19 g of 5% Pd-C and the mixture was reduced similarly to Example 19. Thereafter the same procedure as Example 19 was followed to obtain 0.64 g (95% yield) of (+)-4'-(1-hexanoyloxyethyl)-4-biphenylcarboxylic acid. $[\alpha]_D^{25} = +69°$ (c=1, CHCl₃), m.p.=133°-135° C.

EXAMPLE 26

15 g of benzyl (−)-4'-(1-acetoxyethyl)-4-biphenylcarboxylate, 10 ml of chloroform, 400 ml of 0.2M phosphate buffer and 3 g of Amano swine liver esterase were mixed and reacted at 30°-35° C. for 30 hours. The reaction solution was extracted with chloroform. The chloroform layer was concentrated and the residue was column-chromatographed to give 11.8 g of (−)-benzyl 4'-(1-hydroxyethyl)-4-biphenylcarboxylate (V-26).

1.00 g (3 mmol) of V-26, 15 ml of dichloromethane, 0.37 g (3.6 mmol) of 2s-methylbutanoic acid (VI-26), 0.67 g (3.3 mmol) of dicyclohexylcarbodiimide and 0.02 g of 4-pyrrolidinopyridine were reacted at 20°-25° C. for 12 hours. The insolubles were filtered out and the filtrate was concentrated. The residue was purified by column chromatography to obtain 2(s)-methylbutanoic ester of (−)-benzyl 4'-(1-hydroxyethyl)-4-biphenylcarboxylate (VII-26) in a 95% yield. $[\alpha]_D^{25} = -63°$ (c=1, chloroform), $n_D^{25} = 1.5564$.

A mixed solution of 0.83 g (2 mmol) of VII-26, 10 ml of tetrahydrofuran, 2 ml of methanol and 0.17 g of 5% Pd-C was hydrogenated under normal pressure. After the reaction, the catalyst was filtered out and the filtrate was subjected to the same treatments and purification as in Example 25 to obtain 0.62 g (95.5% yield) of (−)-4'-(1-(2(s)-methylbutanoyloxy)ethyl)-4-biphenylcarboxylic acid. $[\alpha]_D^{20} = -77°$ (c=1, chloroform), m.p.=1° C.

EXAMPLE 27

36.5 g (0.1 mol) of p-chlorobenzyl 4'-acetyl-4-biphenylcarboxylate, 150 ml of chloroform and 50 ml of ethanol were supplied into a four-necked flask equipped with a stirrer and a thermometer. Then 3.8 g (0.1 mol) of sodium borohydride was added at 15°-25° C. over a period of 10 minutes. The mixture was maintained at the same temperature for 2 hours. The reaction mixture was poured into ice-water and extracted twice with 200 ml of ethyl acetate. The organic layer was washed with water and concentrated under reduced pressure to obtain 36.5 g (99.5% yield) of p-chlorobenzyl 4'-(1-hydroxyethyl)-4-biphenylcarboxylate (III-27).

33.0 g (0.09 mol) of III-27 was dissolved in a mixed solution of 150 ml of toluene and 50 ml of pyridine, followed by addition of 9.42 g (0.12 mol) of acetyl chloride at 15°-20° C. over a period of 2 hours. The mixture was maintained at the same temperature for one hour and then at 40°-50° C. for 2 hours. The reaction mixture was cooled below 10° C. and added with 300 ml of 3N hydrochloric acid. After separating the liquid phase, the organic layer was washed with water. 5% sodium hydrogencarbonate and water successively in that order and concentrated under reduced pressure. The residue was purified by column chromatography to obtain 36.4 g (99.0% tield) of p-chlorobenzyl 4'-(1-acetoxyethyl)-4-biphenylcarboxylate (IV-27).

32.7 g (0.08 mol) of IV-27 was mixed with 800 ml of 0.1M phosphate buffer (pH 7.5), 30 ml of chloroform and 6.0 g of Amano Lipase P, and the mixture was stirred vigorously at 40°-45° C. for 20 hours. The reaction mixture was extracted with 600 ml of methyl isobutyl ketone. The organic layer was concentrated under reduced pressure and the residue was subjected to column chromatography using a 12:1 mixed solution of hexane and ethyl acetate as eluting solvent to obtain 13.8 g of (+)-p-chlorobenzyl 4'-(1-hydroxyethyl)-4-biphenylcarboxylate (V-27). $[\alpha]_D^{20} = +21.7°$ (c=0.544, CHCl₃), m.p.=108°-110.5° C.

1.00 g (3 mmol) of V-27 was mixed with 10 ml of pyridine and 10 ml of dichloromethane. The mixture was further added with 0.31 g (3.3 mmol) of propionic acid chloride and reacted at 20°-25° C. for 3 hours and then at 40°-45° C. for 3 hours. The reaction mixture was treated and purified according to Example 25 to obtain 1.12 g of propionic acid ester of (+)-p-chlorobenzyl 4'-(1-hydroxyethyl)-4-biphenylcarboxylate (VII-27) in a 97% yield. $[\alpha]_D^{25} = +28°$ (c=1, CHCl₃).

0.78 g (2 mmol) of VII-27 was dissolved in 20 ml of tetrahydrofuran and the mixture was hydrogenated under normal pressure by using 0.1 g of 5% Pd-C. The reaction mixture was treated and purified according to Example 19 to obtain 0.58 g (96.5% yield) of (+)-4'-(1-propionyloxyethyl)-4-biphenylcarboxylic acid. $[\alpha]_D^{25} = +89°$ (c=1, CHCl₃), m.p.=175°-176° C.

EXAMPLES 28-30

The procedure of Example 20 was followed except that (−)-benzyl 4-(1-hydroxyethyl)phenylcarboxylate (V-20) was used as a starting material and that 4.8 mmol of carboxylic acids shown in Table 1 were used in place of 2(s)-methylbutanoic acid. The results are shown in Table 1.

TABLE 1

| Example No. | Carboxylic acid (VI) used | | Compound of formula (VII) | | Produced compound of formula (I) (l = 1, m = 1) | | |
|---|---|---|---|---|---|---|---|
| | Name | R₂ | Yield | Property values | R₂ | Yield | Property values |
| 28 | Decanoic acid | C₉H₁₉— | 93% | $[\alpha]_D^{25}$ −46.5°* $n_D^{25}$ 1.5182 | C₉H₁₉— | 94.5% | $[\alpha]_D^{25}$ −59°* $n_D^{25}$ 1.4801 |
| 29 | (2s,3s)-2-chloro-3-methylpentanoic acid | C₂H₅—CH—CH—             \|    \|             CH₃ Cl             (S)  (S) | 96.5% | $[\alpha]_D^{25}$ −59.5°* $n_D^{25}$ 1.5353 | C₂H₅—CH—CH            \|    \|            CH₃ Cl            (S) (S) | 33% | $[\alpha]_D^{25}$ −76°* $n_D^{25}$ 1.5140 |

TABLE 1-continued

| Example No. | Carboxylic acid (VI) used | | Compound of formula (VII) | | Produced compound of formula (I) (l = 1, m = 1) | | |
|---|---|---|---|---|---|---|---|
| | Name | $R_2$ | Yield | Property values | $R_2$ | Yield | Property values |
| 30 | 2(s)-chloro-propionic acid | Cl<br>\|<br>$CH_3$—CH—<br>(S) | 94% | $[\alpha]_D^{25}$ −61°*<br>$n_D^{25}$ 1.5403 | Cl<br>\|<br>$CH_3$—CH—<br>(S) | 32% | $[\alpha]_D^{25}$ −96°*<br>$n_D^{25}$ 1.5126 |

*(c = 1, CHCl$_3$)

EXAMPLES 31 and 32

The procedure of Example 26 was followed except that (−)-benzyl 4′-(1-hydroxyethyl)-4-biphenylcarboxylate (V-26) was used as starting material and that 3.6 mmol of carboxylic acids shown in Table 2 were used in place of 2(s)-methylbutanoic acid (VI-26) to obtain the results shown in Table 2.

a column chromatography to obtain 3.08 g of (+)-methyl 4-(1-dodecyloxyethyl)benzoate (VII-33). Yield: 88.5%, $n_D^{20}$=1.4762, $[\alpha]_D^{20}$+29.6° (c=1, CHCl$_3$).

A mixture of 2.08 g (6 mmol) of (VII-33) as obtained above, 10 ml of methanol and 7.5 g of 10% sodium hydroxide was stirred at a temperature of 25°–30° C. for 5 hours. After completion of the reaction, methanol was

TABLE 2

| Example No. | Carboxylic acid (VI) used | | Compound of formula (VII) | | Produced compound of formula (I) (l = 2, m = 1) | | |
|---|---|---|---|---|---|---|---|
| | Name | $R_2$ | Yield | Property values | $R_2$ | Yield | Property values |
| 31 | Decanoic acid | $C_9H_{19}$ | 94% | $[\alpha]_D^{25}$ −33°*<br>$n_D^{25}$ 1.5388 | $C_9H_{19}$ | 96.5% | $[\alpha]_D^{25}$ −53°*<br>M.p. = 128–130° C. |
| 32 | (2s, 3s)-2-chloro-3-methylpentanoic acid | $CH_3$ Cl<br>\| \|<br>$C_2H_5$—CH—CH<br>(S) (S) | 93% | $[\alpha]_D^{25}$ −35°*<br>$n_D^{25}$ 1.5800 | $CH_3$ Cl<br>\| \|<br>$C_2H_5$—CH—CH—<br>(S) (S) | 40% | $[\alpha]_D^{20}$ −70°*<br>M.p. = 150° C. |

*(c = 1, CHCl$_3$)

EXAMPLE 33

1.8 g (10 mmol) of (+)-methyl 4-(1-hydroxyethyl)-benzoate (V-1) obtained in Example 1 was dissolved in 30 ml of dimethylformamide and then cooled to 10° C. 0.3 g (13 mmol) of sodium hydride was added thereto and stirred at a temperature of 30°–35° C. for a hour. Then, 4.8 g (14 mmol) of n-dodecyl tosylate was added at a temperature of 20°–25° C., and thereafter stirred at 40° C. for 3 hours. After completion of the reaction, the reaction mixture was poured into ice-water and then subjected to extraction-treatment with 100 ml of ether. The organic layer was water-washed and then concentrated in vacuo. The residue was then purified through distilled out, and then the residue was weakly acidified with 10% aqueous hydrochloric acid and extracted with 30 ml of ethyl acetate. The organic layer was water-washed, concentrated in vacuo and then purified through a chromatography to obtain 1.88 g of (+)-4-(1-dodecyloxyethyl)benzoic acid (I-33). m.p. 49°–50° C., $[\alpha]_D^{20}$+32° (c=1, CHCl$_3$).

EXAMPLES 34–38

The procedures of Example 33, except that the alkylating reagents shown in Table 3 were used in place of n-dodecyl tosylate, were followed by the alkylation, hydrolysis and after-treatment. The results were obtained as shown in Table 3.

TABLE 3

| Example | Alkylating reagent (VI) | | Compound of the general formula (VII) | | Compound of the general formula (I) | | | |
|---|---|---|---|---|---|---|---|---|
| | Name of compound | Amount used | Amount yielded (% Yield) | Value of physical properties | $R_2$ | l | m | Yield | Value of physical properties |
| 34 | (S)-2-methylbutyl tosylate | 3.4 g (14 mmol) | 2.32 g (92.5%) | $[\alpha]_D^{20}$ +45.5°<br>(c = 1, CHCl$_3$)<br>$n_D^{20}$ 1.4709 | $CH_3$<br>\|<br>$C_2H_5$CHCH$_2$—<br>* | 1 | 0 | 90% | $[\alpha]_D^{20}$ +47.3°<br>(c = 1, CHCl$_3$)<br>$n_D^{20}$ 1.4718 |
| 35 | Methoxyethyl tosylate | 3.2 g (14 mmol) | 2.09 g (88%) | $[\alpha]_D^{20}$ +48.5°<br>(c = 1, CHCl$_3$)<br>$n_D^{20}$ 1.4948 | $CH_3OCH_2CH_2$— | 1 | 0 | 88% | $[\alpha]_D^{20}$ +60.4°<br>(c = 1, CHCl$_3$)<br>$n_D^{20}$ 1.5088 |
| 36 | 2-chloropropyl tosylate | 3.73 g (15 mmol) | 1.54 g (60%) | $[\alpha]_D^{20}$ +58.2°<br>(c = 1, CHCl$_3$)<br>$n_D^{20}$ 1.4972 | Cl<br>\|<br>$CH_3CHCH_2$— | 1 | 0 | 86% | $[\alpha]_D^{20}$ +61°<br>(c = 1, CHCl$_3$)<br>$n_D^{20}$ 1.5116 |
| 37 | 2-fluoroethyl tosylate | 3.27 g (15 mmol) | 1.47 g (65%) | $[\alpha]_D^{20}$ +60.4°<br>(c = 1, CHCl$_3$)<br>$n_D^{20}$ 1.4941 | F—$CH_2CH_2$— | 1 | 0 | 85% | $[\alpha]_D^{20}$ +66.5°<br>(c = 1, CHCl$_3$)<br>$n_D^{20}$ 1.5071 |
| 38 | Octadecyl tosylate | 5.1 g (12 mmol) | 3.59 g (83%) | $[\alpha]_D^{20}$ +19.8°<br>(c = 1, CHCl$_3$) | $CH_3(CH_2)_{17}$— | 1 | 0 | 92% | $[\alpha]_D^{20}$ +23.2°<br>(c = 1, CHCl$_3$) |

EXAMPLE 39

The procedure of Example 1, except that 44.0 g (0.2 mol) of butyl 4-acetyl benzoate is used in place of methyl 4-acetyl benzoate followed by the reaction, after-treatment etc. to obtain 16.6 g of (+)-butyl 4-(1-hydroxyethyl)benzoate (V-39). $[\alpha]_D^{20} = +36°$ (c=1, CHCl$_3$).

2.22 g (10 mmol) of (V-39) as obtained above was dissolved into 30 ml of dimethylformamide and cooled to 10° C. Then, was added thereto 0.48 g (12 mmol) of sodium hydride, and maintained at a temperature of 30°-40° C. for a hour. Further, 4.4 g (14 mmol) of n-decyl tosylate was added thereto at a temperature of 20°-25° C. and reacted at 40° C. for 5 hours. After completion of the reaction, the reaction mixture was poured into ice-water and subjected to extraction treatment with 100 ml of toluene. The organic layer was water-washed to concentrate under a reduced pressure. The residue of the concentration was purified through a column chromatography to obtain 3.22 g of (+)-butyl 4-(1-decyloxyethyl)benzoate (VII-39). Yield: 89%. $[\alpha]_D^{20}$ +29.3° (c=1, CHCl$_3$), $n_D^{20}$ =1.4758.

In the next place, a mixture of 2.17 g (6 mmol) of (VII-39) as obtained above, 10 ml of tetrahydrofuran and 5 g of 10% sodium hydroxide is stirred at a temperature of 25°-30° C. for 5 hours. The after-treatment and purification was conducted in accordance with those of Example 33 to obtain 1.67 g of (+)-4-(1-decyloxyethyl)-benzoic acid (I-39) with yield of 91%. m.p. 56.5°-57.5° C., $[\alpha]_D^{20}$ +37.5° (c=1, CHCl$_3$).

EXAMPLE 40

2.22 g (10 mmol) of (V-39) obtained in Example 39 was used. According to Example 39 except of using 4.32 g (15 mmol) of 2-fluoroheptyl tosylate in place of n-decyl tosylate, alkylation reaction, after-treatment and then purification were carried out to obtain 2.37 g of (+)-butyl 4-(1-(2'-fluoroheptyloxy)ethyl)benzoate (VII-40). Yield: 70%, $[\alpha]_D^{20}$ +66.5° (c=1, CHCl$_3$), $n_D^{20}$ 1.4896.

Subsequently, 2.03 g (6 mmol) of (VII-40) was subjected to hydrosis and after-treatment, according to those of Example 39, to obtain (+)-4-(1-(2'-fluoroheptyloxy)ethyl)benzoic acid. $[\alpha]_D^{20}$ +68.7° (c=1, CHCl$_3$) $n_D^{20}$ 1.4967.

We claim:

1. A process for preparing an optically active alcohol of the formula:

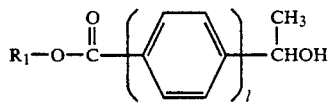

(wherein R$_1$ represents a lower alkyl group or

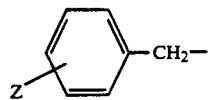

wherein Z represents a hydrogen atom, a halogen atom or a lower alkyl or lower alkoxyl group; l represents a number of 1 or 2; and * indicates asymmetric carbon atom) comprising subjecting an ester represented by the formula:

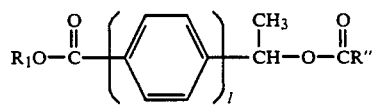

(wherein R$_1$ and l are as defined above, and R" represents a lower alkyl group) to asymmetric hydrolysis by using an esterase having the ability to hydrolyze one of the enantiomers of said ester, said esterase being derived from an animal or a plant and selected from the group consisting of swine liver esterase, steapsin, pancreatin and wheat germ esterase.

2. The process according to claim 1, wherein the asymmetric hydrolysis is carried out in a buffer solution.

3. The process according to claim 1, wherein the asymmetric hydrolysis reaction temperature is 10°-60° C.

4. The process according to claim 2, which is carried out in the presence of an organic solvent.

5. The process according to claim 4, wherein the organic solvent is toluene, chloroform, methyl isobutyl ketone or dichloromethane.

6. A process for producing an optically active alcohol of the formula:

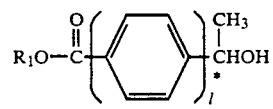

(wherein R$_1$ represents a lower alkyl group or

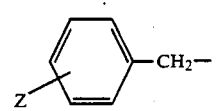

wherein Z represents a hydrogen atom, a halogen atom or a lower alkyl or lower alkoxyl group; l represents a number of 1 or 2; and * indicates asymmetric carbon atom) comprising:

subjecting an ester represented by the formula:

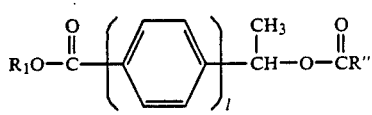

(wherein $R_1$ and $l$ are as defined above, and R'' represents a lower alkyl group to asymmetric hydrolysis by using an esterase having the ability to hydrolyze one of the enantiomers of said ester, said esterase being selected from the group consisting of Lipase P, Lipase AP, Lipase M-AP, Lipase MY, Lipase PL, Lipase AL, Lipase Godo BSL, lipase derived from the Chromobacterium, Talipase, and Lipase Saiken.

7. A process for producing an optically active alcohol of the formula:

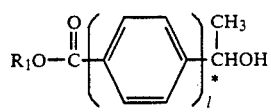

wherein $R_1$ represents a lower alkyl group or

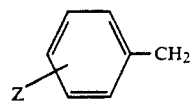

wherein Z represents a hydrogen atom, a halogen atom or a lower alkyl or lower alkoxyl group; $l$ represents a number of 1 or 2; and * indicates asymmetric carbon atom, comprising:

subjecting an ester represented by the formula:

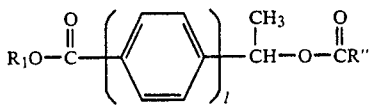

wherein $R_1$ and $l$ are as defined above, and R'' represents a lower alkyl group, to asymmetric hydrolysis by using an esterase having the ability to hydrolyze one of the enantiomers of said ester, said esterase being selected from the group consisting of lipase derived from the Pseudomonas, Lipase P, and lipase derived from the Arthrobactor, Lipase Godo BSL.

8. An optically active alcohol represented by the formula:

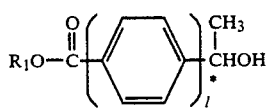

wherein $R_1$ represents a lower alkyl group or

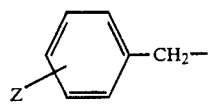

wherein Z represents a hydrogen atom, a halogen atom or a lower alkyl or lower alkoxyl group; $l$ is 1 or 2; and * indicates an asymmetric carbon atom, provided that when $l=1$, $R_1$ is

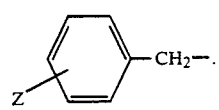

* * * * *